US012751907B2

(12) United States Patent
Kruppa et al.

(10) Patent No.: US 12,751,907 B2
(45) Date of Patent: Oct. 6, 2026

(54) METHOD FOR DYEING KERATINOUS MATERIAL, IN PARTICULAR HUMAN HAIR

(71) Applicant: HENKEL AG & CO. KGAA, Düsseldorf (DE)

(72) Inventors: Carolin Kruppa, Hilden (DE); Torsten Lechner, Langenfeld (DE); Marc Nowottny, Mönchengladbach (DE); Carsten Mathiaszyk, Essen (DE); Andreas Walter, Ratingen (DE); Juergen Schoepgens, Schwalmtal (DE); Avni Tairi, Duisburg (DE); Phillip Jaiser, Langenfeld (DE)

(73) Assignee: Henkel AG & Co. KGaA, Düsseldorf (DE)

( * ) Notice: Subject to any disclaimer, the term of this patent is extended or adjusted under 35 U.S.C. 154(b) by 278 days.

(21) Appl. No.: 18/686,797

(22) PCT Filed: Jul. 12, 2022

(86) PCT No.: PCT/EP2022/069408
§ 371 (c)(1),
(2) Date: Feb. 26, 2024

(87) PCT Pub. No.: WO2023/025452
PCT Pub. Date: Mar. 2, 2023

(65) Prior Publication Data

US 2024/0350389 A1 Oct. 24, 2024

(30) Foreign Application Priority Data

Aug. 26, 2021 (DE) ..................... 10 2021 209 370.1

(51) Int. Cl.
*A61Q 5/10* (2006.01)
*A61K 8/58* (2006.01)

(52) U.S. Cl.
CPC ................ *A61K 8/585* (2013.01); *A61Q 5/10* (2013.01); *A61K 2800/4324* (2013.01); *A61K 2800/48* (2013.01); *A61K 2800/884* (2013.01)

(58) Field of Classification Search
CPC ............ A61K 8/585; A61K 2800/4324; A61K 2800/48; A61K 2800/884; A61Q 5/10; A61Q 5/065
USPC .............................................................. 8/405
See application file for complete search history.

(56) References Cited

U.S. PATENT DOCUMENTS

| | | | | |
|---|---|---|---|---|
| 2010/0083446 A1* | 4/2010 | Brun | ...................... | A61K 8/891 8/405 |
| 2019/0060196 A1 | 2/2019 | Elsen et al. | | |
| 2023/0059044 A1 | 2/2023 | Krohn et al. | | |

FOREIGN PATENT DOCUMENTS

| | | | |
|---|---|---|---|
| WO | WO 2020187732 A1 * | 9/2020 | ............. A61K 8/585 |
| WO | WO 2020187736 A1 * | 9/2020 | ........... A61K 8/8147 |
| WO | 2021/121723 A1 | 6/2021 | |

OTHER PUBLICATIONS

International Search Report issued in PCT/EP2022/069408 dated Dec. 5, 2022.
Written Opinion issued in PCT/EP2022/069408 dated Dec. 5, 2022.

* cited by examiner

*Primary Examiner* — Eisa B Elhilo
(74) *Attorney, Agent, or Firm* — Blank Rome LLP

(57) ABSTRACT

A method for dyeing keratinous material, such as human hair, is described. Initially, a first agent is applied to the keratinous material. The first agent includes less than 10 wt % water, at least one organic silicon compound selected from the group comprising silanes having one, two, or three silicon atoms, and at least one chromophoric compound. A second agent is applied to the keratinous material which is still impinged with first agent. The second agent includes water. The first and second agents are allowed to act upon the keratinous material. The first and second agents are then rinsed.

20 Claims, No Drawings

METHOD FOR DYEING KERATINOUS MATERIAL, IN PARTICULAR HUMAN HAIR

CROSS-REFERENCE TO RELATED APPLICATIONS

This application is a National Stage of International Patent Application No. PCT/EP2022/069408, filed Jul. 12, 2022, which claims foreign priority to German Patent Application No. 10 2021 209 370.1, filed Aug. 26, 2021, the disclosures of which are hereby incorporated by reference herein in their entireties.

FIELD OF THE INVENTION

The subject matter of the present application is a method for coloring keratinous material, and in particular human hair, which comprises the application of two agents (a) and (b). The agent (a) is water-poor or anhydrous and is characterized by its content of at least one organic silicon compound and a chromophoric compound. The agent (a) is first applied to the keratinous material or the hair. Thereafter, the water-containing agent (b) is added to the keratinous material or hair which is still impinged with agent (a), wherein the water contained in agent (b) leads to a targeted hydrolysis of the silicon compounds upon contact with agent (a). After allowing the two agents (a) and (b) to act, they are then rinsed out together.

BACKGROUND

Changing the shape and color of keratinous fibers, in particular hair, represents an important area of modern cosmetics. To change the hair color, a person skilled in the art is familiar with a variety of dyeing systems depending upon the dyeing requirements. Oxidation dyes are typically used for permanent, intense dyeing with good fastness properties and good gray coverage. Such dyes typically contain oxidation dye precursors, known as developer components, and coupler components, which together form the actual dyes under the influence of oxidizing agents—for example, hydrogen peroxide. Oxidation dyes are characterized by very long-lasting color results.

When using direct dyes, dyes that are already fully formed diffuse from the dye into the hair fiber. In comparison with oxidative hair coloring, the colors obtained with direct dyes have a lower durability and a more rapid washing out. Colorations with direct dyes typically remain on the hair for a period of between 5 and 20 hair washes.

For short-term color changes on the hair and/or the skin, the use of color pigments is known. Color pigments are generally understood to mean insoluble dyeing substances. These are present in the form of small particles in the dye formulation and are deposited only from the outside onto the hair fibers and/or the skin surface. Therefore, they can generally be removed again without residue by a few washes using surfactant-containing cleaning agents. Various products of this type are available on the market under the name, "hair mascara."

If the user desires particularly long-lasting colors, the use of oxidative coloring agents has hitherto been the only option. However, despite multiple optimization attempts, an unpleasant ammonia odor or amine odor cannot be completely avoided in oxidative hair dyeing. The hair damage that remains associated with the use of the oxidative coloring agents also has a disadvantageous effect on the hair of the user. The search for alternative, high-performance dyes and dyeing methods is therefore an ongoing challenge. The focus is in particular on coloring systems in which the chromophoric compounds are integrated into a film and attached on the surface of the hair fiber so that, at the request of the user, they can be removed again without residue and without changing the original hair color.

EP 2168633 B1 addresses the task of producing long-lasting hair dyes using pigments. The document teaches that, when using a combination of a pigment, an organic silicon compound, a film-developing polymer, and a solvent on hair, dyes can be produced which are particularly resistant to abrasion and being shampooed.

The great advantage of alkoxy silanes used in EP 2168633 B1 is that the high reactivity of this compound class enables very rapid coating. Thus, extremely good dyeing results can be achieved even after very brief application periods of only a few minutes. However, in addition to these advantages, the high reactivity of the alkoxy silanes also entails some disadvantages.

The organic silicon compounds used in the dyes are highly reactive compounds which undergo hydrolysis or oligomerization and/or polymerization in the presence of water. It is important to adjust the rate of oligomerization or polymerization in such a way that it enables the application of the coloring agent within a time frame acceptable for the user.

Due to their high reactivity, the organic alkoxy silanes cannot be prepared together with larger amounts of water, because a large excess of water initiates the immediate hydrolysis and subsequent polymerization. The polymerization taking place during storage of the alkoxy silanes in aqueous medium is manifested in thickening or gelling of the aqueous preparation. As a result, the preparations are so highly viscous, gel-like, or gelatinous that they can no longer be applied uniformly on the keratinous material. In addition, the storage of the alkoxy silanes in the presence of high amounts of water is associated with a loss of their reactivity, so that the formation of a resistant and uniform coating on the keratinous material is no longer possible. Particularly in the case of dyeing methods, however, the formation of a uniform coating is particularly important.

SUMMARY OF THE INVENTION

For these reasons, it is necessary to store the organic alkoxy silanes in an anhydrous or water-poor environment and to prepare the corresponding preparations in a separate container. The water-poor preparations which contain the alkoxy silanes can also be referred to as "silane blend."

For the application to the keratinous material, the user must now transfer this silane blend into a ready-to-use mixture, so that the formation of the coating is initiated. In the context of the work leading to this invention, the silane blends were mixed with different formulations, and these blends were tested with regard to their performance properties. In a test series, an application mixture with a high water content was produced from the silane blend and a water-containing carrier formulation, and these were applied to strands of hair. In this form of application, the oligomerization or polymerization of the silanes began directly upon contact with the water in the application mixture, which, however, was not yet on the hair. It was found that the color result strongly depends upon the skill of the user and the speed with which he applied the application mixture to the hair. As a result—particularly in the case of slow application, inexperienced first-time users, or large areas of the parts of the hair to be dyed—the hair was dyed very unevenly or insufficiently dyed at certain points.

Accordingly, it is still a great challenge to optimally adapt the polymerization rate, i.e., the rate at which the coating is formed on the keratinous material, to the conditions of use.

It was the object of the present application to find a method for treating keratinous material by means of which the polymerization rate of the organic alkoxy silanes could be adapted to the conditions of use, and in particular to the conditions prevailing during use on the human head. In other words, a method was sought which allows the reproducible formation of a uniformly colored film suitable for dyeing, which results in a uniform coloring on the entire head of the user.

Surprisingly, it has been found that this object can be achieved in full when the keratinous material is treated in a method in which two agents (a) and (b) are successively applied to the keratinous material or the hair. The agent (a) is a water-poor formulation which contains one or more alkoxy silanes and additionally at least one chromophoric compound. Due to the low water content, the oligomerization or polymerization of the alkoxy silanes in agent (a) does not take place or takes place only to a very limited degree. This water-poor and dye-containing agent (a) is now applied to the keratinous material.

In a subsequent step, agent (b) is now applied to the places of the keratinous material on which agent (a) is still located. The agent (b) contains a defined amount of water as an essential component. With the application of agent (b) to the keratinous material, the two agents (a) and (b) are now mixed with one another, which can be supported, for example, by vigorous rubbing or massaging of the keratinous material impinged with the two agents. With the application of agent (b), the alkoxy silanes present in agent (a) are thus in contact with a defined amount of water, so that the oligomerization/polymerization of the silanes is started only at the point in time at which the silanes are already located at the site on the keratinous material or the hair on which the colored film is also to be formed.

DETAILED DESCRIPTION

A first subject matter of the present invention is a method for dyeing keratinous material, and in particular human hair, comprising the following steps in the specified order:

(1) applying an agent (a) to the keratinous material, said agent (a) containing, in relation to the total weight of agent (a):
  - (a1) less than 10 wt % water,
  - (a2) at least one organic silicon compound from the group of silanes having one, two, or three silicon atoms, and
  - (a3) at least one chromophoric compound, (2) applying an agent (b) to the keratinous material, which is still impinged with agent
  - (a), wherein agent (b) contains:
  - (b1) water (3) allowing both agents (a) and (b) to act upon the keratinous material, and (4) rinsing both agents (a) and (b).

It has been shown that when this new method is used on human hair, it has been possible to obtain a reproducible and uniform color result which is also distinguished by intensive color intensities and very good fastnesses. It was particularly advantageous here that the color result was not dependent upon the period of time required by the user for the coloring.

Keratinous Material

Keratinous material is understood to mean hair, the skin, the nails (for example, fingernails and/or toenails). Furthermore, wool, furs, and feathers also fall under the definition of the keratinous material.

Keratinous material is preferably understood to be human hair, human skin, and human nails, and in particular fingernails and toenails. Keratinous material is very particularly preferably understood to mean human hair.

Dyeing of Keratinous Material

In the context of this invention, the phrase, "method for coloring," relates to all those coloring methods in which a colored film is produced on the keratinous material. The coloring of the film can be produced by all those chromophoric compounds which are cosmetically suitable for deposit on the surface of the keratinous materials and can be incorporated into this film. Such chromophoric compounds are, for example, pigments and direct dyes, and very particularly preferably pigments.

Within the scope of the described method, agents (a) and (b) are applied sequentially to the keratinous material, and in particular the human hair. Agents (a) and (b) are each ready-to-use agents. The two agents (a) and (b) are different from each other.

Step (1), Applying Agent (a) to the Keratinous Material

In step (1) of the method according to the invention, the agent (a) is used on the keratinous material, and in particular human hair.

The use of the agent (a) is carried out here, for example, by distributing, or distributing and massaging, the agent (a) onto the keratinous material (or hair) with the aid of the gloved hand, a brush, an applicator bottle, or an applicator. At this point, the keratinous material or the hair is preferably towel-dry or dry.

Dry keratinous material, and in particular dry hair, is the material that does not undergo any additional treatment directly before the coloring method (i.e., up to three hours before the coloring method) and also has not been dampened with water or with water/shampoo.

Towel-dry keratinous material, and in particular towel-dry hair, is designated as the material/hair which was wetted or washed with water within a maximum time of 30 minutes, and preferably 15 minutes, before the start of the coloring process and then rubbed dry with a towel for approx. 30 seconds.

Example: The user completely gets his hair completely wet under the faucet by saturating it completely with water under running water heated to approx. 35° C. Then the user dries the hair for 30 seconds with a dry towel.

Towel-dry hair is characterized by no longer being dripping wet, i.e., there are no longer any significant portions of water on the hair surface. Nevertheless, the hair still has a residual moisture due to the water molecules present within the hair fiber, whereby the hair fibers are swollen. The application of the agent (a) on towel-dry keratinous material, in particular towel-dry hair, is very particularly preferred. The small amount of water present in towel-dry hair facilitates the application and distribution of agent (a), but without any significant oligomerization or polymerization being initiated by too much water.

In the context of a further embodiment, a method according to the invention is characterized in that agent (a) is applied in step (1) to towel-dry or dry keratinous material, and very particularly preferably to towel-dry keratinous material.

In the context of a further embodiment, a method according to the invention is characterized in that agent (a) is applied in step (1) to towel-dry or dry human hair, and very particularly preferably to towel-dry human hair.

Following application to the keratinous material or the hair, agent (a) can still be massaged in. The massaging can be carried out, for example, by mechanical rubbing or scrubbing of the hair with the gloved hand.

Agent (a)

Agent (a) is a ready-to-use agent. It is characterized in that it contains, in relation to the total weight of agent (a), less than 10 wt % water (a1), and at least one organic silicon compound from the group of silanes having one, two, or three silicon atoms (a2) and at least one chromophoric compound (a3).

The agent (a) can be in the form of a liquid, gel, or cream. Thus, agent (a) can be present, for example, in the form of a cream, an emulsion, a gel, or else a surfactant-containing foaming solution, these containing less than 10 wt % water.

Water Content (a1) in Agent (a)

In relation to the total weight of agent (a), this contains less than 10 wt % water. This ensures that agent (a) remains stable over the entire application period, and premature, undesired oligomerization or polymerization of the silanes can be avoided to a sufficient extent. Even if the stability of the agent can already be ensured at a water content of up to 10 wt %, to further optimize the stability and the color intensities, it has been found preferable to adjust the water content of agent (a) to a value below 10 wt %. In this way, particularly good results were obtained if the water content in agent (a)—in relation to the total weight of agent (a)—was 0 to 7.5 wt %, preferably 0.0 to 5.0 wt %, further preferably 0.0 to 4.0 wt %, and very particularly preferably 0 to 2.5 wt %.

In the context of a further very particularly preferred embodiment, a method according to the invention is characterized in that agent (a)—in relation to the total weight of agent (a)—contains 0 to 7.5 wt %, preferably 0.0 to 5.0 wt %, further preferably 0.0 to 4.0 wt %, and very particularly preferably 0 to 2.5 wt %, water (a1).

The range of 0 to 2.5 wt % water means that the agent contains as little water as possible, or else the amount of water which is in some cases introduced into agent (a) by further ingredients contained in agent (a) does not exceed a content of 2.5 wt %.

Organic Silicon Compounds from the Group of Silanes (a2) in Agent (a)

As a second ingredient essential to the invention (a2), agent (a) contains at least one organic silicon compound from the group of silanes having one, two, or three silicon atoms.

Especially preferably, agent (a) contains at least one organic silicon compound (a1) selected from silanes having one, two, or three silicon atoms, wherein the organic silicon compound comprises one or more hydroxyl groups and/or hydrolyzable groups per molecule.

These organic silicon compounds (a1) or organic silanes contained in agent (a) are reactive compounds.

Organic silicon compounds, which are alternatively also referred to as organosilicon compounds, are compounds which either have a direct silicon-carbon bond (Si—C) or in which the carbon is linked to the silicon atom via an oxygen, nitrogen, or sulfur atom. The organic silicon compounds according to the invention are compounds which contain one to three silicon atoms. The organic silicon compounds particularly preferably contain one or two silicon atoms.

According to the IUPAC rules, the designation, "silane," denotes a substance group of chemical compounds based upon a silicon backbone and hydrogen. In the case of organic silanes, the hydrogen atoms are replaced, completely or in part, by organic groups such as (substituted) alkyl groups and/or alkoxy groups. Some of the hydrogen atoms can also be replaced by hydroxyl groups in the organic silanes.

In the context of a particularly preferred embodiment, a method is characterized by the use of an agent (a) on the keratinous material, wherein agent (a) contains at least one organic silicon compound (a1) selected from silanes having one, two, or three silicon atoms, wherein the organic silicon compound also comprises one or more hydroxyl groups or hydrolyzable groups per molecule.

In the context of a very particularly preferred embodiment, a method according to the invention is characterized by the use of an agent on the keratinous material, wherein agent (a) contains at least one first organic silicon compound (a1) selected from silanes having one, two, or three silicon atoms, wherein the organic silicon compound also comprises one or more basic chemical functions and one or more hydroxyl groups or hydrolyzable groups per molecule.

This basic group or basic chemical function may, for example, be an amino group, an alkylamino group, a dialkylamino group, or a trialkylamino group, which is preferably bonded to a silicon atom via a linker. Preferably, the basic group is an amino group, a $C_1$-$C_6$ alkylamino group, or a Di($C_1$-$C_6$) alkylamino group.

The hydrolyzable group(s) is/are preferably a $C_1$-$C_6$ alkoxy group, and in particular an ethoxy group or a methoxy group. It is preferred if the hydrolyzable group is present directly bound to the silicon atom. If, for example, the hydrolyzable group is an ethoxy group, the organic silicon compound preferably contains a structural unit R'R"R'"Si—O—CH2-CH3. The R', R", and R'" functional groups here represent the three remaining free valencies of the silicon atom.

A very particularly preferred method is characterized in that agent (a) contains at least one organic silicon compound selected from silanes having one, two, or three silicon atoms, wherein the organic silicon compound preferably comprises one or more basic chemical functions and one or more hydroxyl groups or hydrolyzable groups per molecule.

It was possible to obtain very excellent results when the agent (a) contains at least one organic silicon compound (a1) of formula (I) and/or (II).

The compounds of formulas (I) and (II) are organosilicon compounds selected from silanes with one, two, or three silicon atoms, wherein the organosilicon compound comprises one or more hydroxyl groups and/or hydrolyzable groups per molecule.

In a further very particularly preferred embodiment, the method is characterized in that agent (a) contains at least one organic silicon compound (a2) of the formula (I) and/or (II)

$$R_1R_2N\text{-}L\text{-}Si(OR_3)_a(R_4)_b \qquad (I),$$

in which

- $R_1$, $R_2$ represent, independently of one another, a hydrogen atom or a $C_1$-$C_6$ alkyl group,
- L represents a linear or branched, bivalent $C_1$-$C_{20}$ alkylene group,
- $R_3$, $R_4$ represent, independently of one another, a $C_1$-$C_6$ alkyl group,
- a represents an integer from 1 to 3, and
- b represents the integer 3−a, and where, in the organosilicon compound of formula (II), $$(R_5O)_c(R_6)_dSi\text{-}(A)_e\text{-}[NR_7\text{-}(A')]_f\text{—}[O\text{-}(A'')]_g\text{—}[NR_8\text{-}(A''')]h\text{—}Si(R_6')_d'(OR_5')_{c'} \qquad (II),$$

- R5, R5', R5", R6, R6', and R6" independently of one another represent a $C_1$-$C_6$ alkyl group, A, A', A", A'", and A"" represent, independently of one another, a linear or branched, bivalent $C_1$-$C_{20}$ alkylene group, $R_7$ and $R_8$ represent, independently of one another, a hydrogen atom $C_1$-$C_6$ alkyl group, a hydroxy-$C_1$-$C_6$ alkyl group, a $C_2$-$C_6$ alkenyl group, an amino-$C_1$-$C_6$ alkyl group, or a grouping of the formula (III)

$$(A'''')\text{—}Si(R_6'')_{d''}(OR_5'')_{c''} \quad \text{(III)},$$

c, represents an integer from 1 to 3,
d represents the integer 3−c,
c' represents an integer from 1 to 3,
d' represents the integer 3−c',
c" represents an integer from 1 to 3,
d" represents the integer 3−c",
e represents 0 or 1,
f represents 0 or 1,
g represents 0 or 1,
h represents 0 or 1, with the proviso that at least one of the functional groups e, f, g, and h be different from 0.

The substituents $R_1$, $R_2$, $R_3$, $R_4$, $R_5$, $R_5$', $R_5$", $R_6$, $R_6$', $R_6$", $R_7$, $R_8$, L, A, A', A", A'", and A"" in the compounds of formulas (I) and (II) are explained by way of example below.

Examples of a $C_1$-$C_6$ alkyl group are the methyl, ethyl, propyl, isopropyl, n-butyl, s-butyl and t-butyl, n-pentyl, and n-hexyl groups. Propyl, ethyl, and methyl are preferred alkyl groups. Examples of a $C_2$-$C_6$ alkenyl group are vinyl, allyl, but-2-enyl, but-3-enyl, and isobutenyl; preferred $C_2$-$C_6$ alkenyl functional groups are vinyl and allyl. Preferred examples for a hydroxy-$C_1$-$C_6$ alkyl group are a hydroxy methyl-, a 2-hydroxyethyl-, a 2-hydroxypropyl, a 3-hydroxypropyl-, a 4-hydroxybutyl group, a 5-hydroxypentyl-, and a 6-hydroxyhexyl group; a 2-hydroxyethyl group is especially preferred. Examples of an amino-$C_1$-$C_6$ alkyl group are the aminomethyl group, the 2-aminoethyl group, and the 3-aminopropyl group. The 2-aminoethyl group is particularly preferred. Examples of a linear bivalent $C_1$-$C_{20}$ alkylene group are, for example, the methylene group ($-CH_2-$), the ethylene group ($-CH_2-CH_2-$), the propylene group ($-CH_2-CH_2-CH_2-$), and the butylene group ($-CH_2-CH_2-CH_2-CH_2-$). The propylene group ($-CH_2-CH_2-CH_2-$) is especially preferred. Above a chain length of 3 C atoms, bivalent alkylene groups may also be branched. Examples of branched, bivalent $C_3$-$C_{20}$ alkylene groups are ($-CH_2-CH(CH_3)-$) and ($-CH_2-CH(CH_3)-CH_2-$).

In the organosilicon compound of formula (I)

$$R_1R_2N\text{-}L\text{-}Si(OR_3)_a(R_4)_b \quad \text{(I)},$$

the functional groups $R_1$ and $R_2$ represent, independently of one another, a hydrogen atom or a $C_1$-$C_6$ alkyl group. Very particularly preferably, the functional groups $R_1$ and $R_2$ represent a hydrogen atom.

In the central portion of the organic silicon compound is the structural unit or the linker -L-, which represents a linear or branched, bivalent $C_1$-$C_{20}$ alkylene group.

A bivalent $C_1$-$C_{20}$ alkylene group can alternatively also be referred to as a divalent or two-bond $C_1$-$C_{20}$ alkylene group, which means that each L-grouping can enter into two bonds. A bonding takes place from the amino group R1R2N to the linker L, and the second bond is between the linker L and the silicon atom.

Preferably, -L- represents a linear, bivalent $C_1$-$C_{20}$ alkylene group. Further preferably, -L- represents a linear, bivalent $C_1$-$C_6$ alkylene group. Particularly preferably -L- represents a methylene group ($-CH_2-$), an ethylene group ($-CH_2-CH_2-$), a propylene group ($-CH_2-CH_2-CH_2-$), or a butylene group ($-CH_2-CH_2-CH_2-CH_2-$). Very particularly preferably, L represents a propylene group ($-CH_2-CH_2-CH_2-$).

The linear propylene group ($-CH_2-CH_2-CH_2-$) can alternatively also be referred to as a propane-1,3-diyl group.

The organic silicon compounds of formula (I)

$$R_1R_2N\text{-}L\text{-}Si(OR_3)a(R_4)b \quad \text{(I)},$$

each bear one end of the silicon-containing grouping —Si$(OR_3)_a(R_4)_b$.

In the terminal structural unit —Si$(OR_3)_a(R_4)_b$, the functional group $R_3$ represents a hydrogen atom or a $C_1$-$C_6$ alkyl group, and the functional group $R_4$ represents a $C_1$-$C_6$ alkyl group. Particularly preferably $R_3$ and $R_4$ represent, independently of one another, a methyl group or an ethyl group.

In this case, a represents an integer from 1 to 3, and b represents the integer 3−a. If a represents the number 3, then b equals 0. If a represents the number 2, then b is equal to 1. If a represents the number 1, then b is equal to 2.

It was possible to produce especially resistant films when the agent (a) contains at least one first organic silicon compound (a2) of formula (I), wherein the functional groups $R_3$, $R_4$ represent, independently of one another, a methyl group or an ethyl group.

When the method for coloring human hair was used, it was possible to obtain colorings having the best wash-fastness if agent (a) contains at least one organic silicon compound (a2) of the formula (I), in which the functional groups $R_3$, $R_4$ independently of one another represent a methyl group or an ethyl group.

Furthermore, it was possible to obtain colors having the best wash-fastness when the agent (a) contains at least one organic silicon compound of formula (I), wherein the functional group a represents the number 3. In this case, the group b represents the number 0.

In another preferred embodiment, the agent (a) used in the method is characterized in that it contains at least one organic silicon compound (a2) of the formula (I) wherein, $R_3$, $R_4$ represent, independently of one another, a methyl group or an ethyl group, and
a represents the number 3, and
b represents the number 0.

In a further preferred embodiment, a method according to the invention is characterized in that the agent (a) contains at least one first organic silicon compound (a2) of the formula (I), $$R_1R_2N\text{-}L\text{-}Si(OR_3)_a(R_4)_b \quad \text{(I)},$$

in which $R_1$, $R_2$ both represent a hydrogen atom, and
L represents a linear, bivalent $C_1$-$C_6$ alkylene group—preferably a propylene group ($-CH_2-CH_2-CH_2-$) or an ethylene group ($-CH_2-CH_2-$),
$R_3$ represents a hydrogen atom, an ethyl group, or a methyl group,
$R_4$ represents a methyl group or an ethyl group,
a represents the number 3, and
b represents the number 0.

To achieve the object according to the invention, particularly well-suited organic silicon compounds of formula (I) are:

(3-aminopropyl)triethoxysilane,

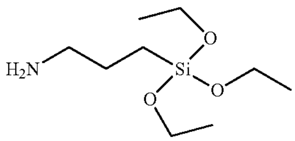

(3-aminopropyl)trimethoxysilane,

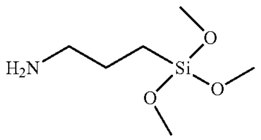

1-(3-aminopropyl)silanetriol,

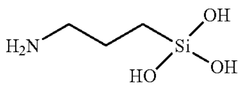

(2-aminoethyl)triethoxysilane,

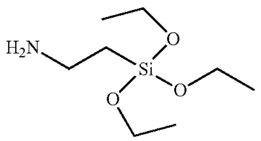

(2-aminoethyl)trimethoxysilane,

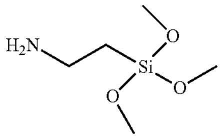

1-(2-aminoethyl)silanetriol,

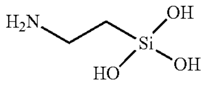

(3-dimethylaminopropyl)triethoxysilane,

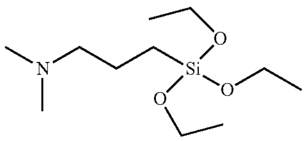 [SMILES: CCO[Si](CCCN(C)C)(OCC)OCC]

(3-dimethylaminopropyl)trimethoxysilane,

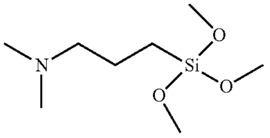

1-(3-dimethylaminopropyl)silanetriol,

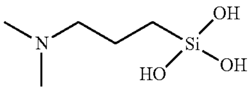

(2-dimethylaminopropyl)triethoxysilane,

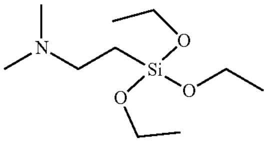

(2-dimethylaminoethyl)trimethoxysilane, and

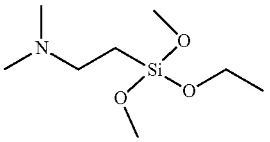

1-(2-dimethylaminoethyl)silanetriol.

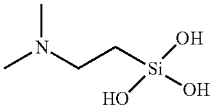

In a further preferred embodiment, a method according to the invention is characterized in that the agent (a) contains at least one organic silicon compound (a2) of formula (I), which is selected from the group consisting of
(3-aminopropyl)triethoxysilane,
(3-aminopropyl)trimethoxysilane,
1-(3-aminopropyl)silanetriol,
(2-aminoethyl)triethoxysilane,
(2-aminoethyl)trimethoxysilane,
1-(2-aminoethyl)silanetriol,
(3-dimethylaminopropyl)triethoxysilane,
(3-dimethylaminopropyl)trimethoxysilane,
1-(3-dimethylaminopropyl)silanetriol,
(2-dimethylaminoethyl)triethoxysilane,
(2-dimethylaminoethyl)trimethoxysilane, and/or
1-(2-dimethylaminoethyl)silanetriol.

The aforementioned organic silicon compounds of the formula (I) are commercially available. (3-aminopropyl)trimethoxysilane can be purchased from Sigma-Aldrich, for example. Also, (3-aminopropyl)triethoxysilane can be purchased from Sigma-Aldrich.

In the context of another embodiment, the agent contains at least one organic silicon compound (a2) of the formula (II)

$$(R_5O)_c(R_6)_dSi\text{-}(A)_e\text{-}[NR_7\text{-}(A')]_f\text{—}[O\text{-}(A'')]_g\text{—}[NR_8\text{-}(A''')]_h\text{—}Si(R_6')_{d'}(OR_5')_{c'} \quad \text{(II).}$$

The silicon organic compounds of formula (II) each bear the silicon-containing groups $(R_5O)_c(R_6)_dSi$— and —$Si(R_6')_{d'}(OR_5')_{c'}$ at their two ends.

Located in the middle part of the molecule of the formula (II) are the groups $-(A)_e-$ and $[NR_7-(A')]_f-$ and $—[O-(A'')]_g-$ and $—[NR_8-(A''')]_h-$. Here, each of the functional groups e, f, g, and h can, independently of one another, represent the number 0 or 1, wherein there is the proviso that at least one of the functional groups e, f, g, and h be different from 0. In other words, an organic silicon compound of the formula (II) contains at least one grouping from the group consisting of $-(A)_e-$ and $—[NR_7-(A')]-$ and $—[O-(A'')]-$ and $—[NR_8-(A''')]-$.

In the two terminal structural units $(R_5O)_c(R_6)_dSi$— and —$Si(R_6')_{d'}(OR_5')_{c'}$, the functional groups R5, R5', R5'' represent, independently of one another, one hydrogen atom or a $C_1$-$C_6$ alkyl group. The functional groups R6, R6', and R6'' represent, independently of one another, a $C_1$-$C_6$ alkyl group.

Here, c represents an integer from 1 to 3, and d represents the whole number 3−c. If c represents the number 3, then d is equal to 0. If c represents the number 2, then d is equal to 1. If c represents the number 1, then d is equal to 2.

Similarly, c' represents an integer from 1 to 3, and d' represents the integer 3−c'. If c' represents the number 3, then d' is equal to 0. If c' represents the number 2, then d' is equal to 1. If c' represents the number 1, then d' is equal to 2.

It was possible to obtain films having the highest stability or dyes having the best wash-fastness when the groups c and c' both represent the number 3. In this case, d and d' both represent the number 0.

In a further preferred embodiment, a method is characterized in that agent (a) contains at least one organic silicon compound (a2) of the formula (II), $$(R_5O)_c(R_6)_dSi\text{-}(A)_e\text{-}[NR_7\text{-}(A')]_f\text{—}[O\text{-}(A'')]_g\text{—}[NR_8\text{-}(A''')]_h\text{—}Si(R_6')_{d'}(OR_5')_{c'} \quad \text{(II),}$$

in which

R5 and R5' represent, independently of one another, a methyl group or an ethyl group, c and c' both represent the number 3, and d and d' both represent the number 0.

If c and c' both represent the number 3, and d and d' both represent the number 0, the organic silicon compound according to the invention corresponds to the formula (IIa)

$$(R_5O)_3Si\text{-}(A)_e\text{-}[NR_7\text{-}(A')]_f\text{—}[O\text{-}(A'')]_g\text{—}[NR_8\text{-}(A''')]_h\text{—}Si(OR_5')_3 \quad \text{(IIa).}$$

The functional groups e, f, g, and h can represent, independently of one another, the number 0 or 1, wherein at least one functional group of e, f, g, and h is different from zero. The abbreviations, e, f, g, and h, define which of the groupings $-(A)_e-$ and $—[NR_7-(A')]_f-$ and $—[O-(A'')]_g-$ and $—[NR_8-(A''')]h-$ are located in the middle part of the organic silicon compound of formula (II).

In this context, the presence of certain groupings has proven to be particularly advantageous with regard to increasing wash-fastness. It was possible to obtain particularly good results when at least two of the functional groups e, f, g, and h represent the number 1. Very particularly preferably, e and f both represent the number 1. Furthermore, very particularly preferably, g and h both represent the number 0.

If e and f both represent the number 1, and g and h both represent the number 0, the organic silicon compound according to the invention corresponds to the formula (IIb)

$$(R_5O)_c(R_6)_dSi\text{-}(A)\text{-}[NR_7\text{-}(A')]\text{—}Si(R_6')_{d'}(OR_5')_{c'} \quad \text{(IIb).}$$

The functional groups A, A', A'', A''', and A'''' represent, independently of one another, a linear or branched, bivalent $C_1$-$C_{20}$ alkylene group. Preferably the functional groups A, A', A'', A''', and A'''' represent, independently of one another, a linear, bivalent $C_1$-$C_{20}$ alkylene group. More preferably, the functional groups A, A', A'', A''', and A'''' represent, independently of one another, a linear, bivalent $C_1$-$C_6$ alkylene group. Particularly preferably, the functional groups A, A', A'', A''', and A'''' represent, independently of one another, a methylene group (—$CH_2$—), an ethylene group (—$CH_2$—$CH_2$—), a propylene group (—$CH_2$—$CH_2$—$CH_2$—), or a butylene group (—$CH_2$—$CH_2$—$CH_2$—$CH_2$—). Very particularly preferably, the functional groups A, A', A'', A''', and A'''' represent a propylene group (—$CH_2$—$CH_2$—$CH_2$—).

The bivalent $C_1$-$C_{20}$ alkylene group can alternatively also be referred to as a divalent or two-bond $C_1$-$C_{20}$ alkylene group, which means that each A, A', A'', A''', and A'''' grouping can have two bonds.

The linear propylene group (—$CH_2$—$CH_2$—$CH_2$—) can alternatively also be referred to as a propane-1,3-diyl group.

If the group f represents the number 1, then the organic silicon compound of the formula (II) contains a structural grouping —$[NR_7-(A')]$-.

If the functional group h represents the number 1, then the organic silicon compound of the formula (II) contains a structural grouping —$[NR_8-(A''')]$-.

In this context, $R_7$ and $R_8$ represent, independently of one another, a hydrogen, a $C_1$-$C_6$ alkyl group, a hydroxy-$C_1$-$C_6$ alkyl group, a $C_2$-$C_6$ alkenyl group, an amino-$C_1$-$C_6$ alkyl-group, or a grouping of formula (III)

$$\text{-}(A'''')\text{—}Si(R_{e}'')_{d}''(OR_5'')_c'' \quad \text{(III).}$$

Most preferably, the functional groups R7 and R8 represent, independently of one another, a hydrogen atom, a methyl group, a 2-hydroxyethyl group, a 2-alkenyl group, a 2-aminoethyl group, or a grouping of formula (III).

If the functional group f represents the number 1, and the functional group h represents the number 0, the organic silicon compound contains the grouping $[NR_7-(A')]$, but not the grouping —$[NR_8-(A'')]$. If the functional group R7 represents a group of formula (III), the agent (a) contains an organic silicon compound having 3 reactive silane groups.

In a further preferred embodiment, a method is characterized in that agent (a) contains at least one organic silicon compound (a2) of the formula (II), $$(R_5O)_c(R_6)_dSi\text{-}(A)_e\text{-}[NR_7\text{-}(A')]_f\text{—}[O\text{-}(A'')]_g\text{—}[NR_8\text{-}(A''')]_h\text{—}Si(R_6')_{d'}(OR_5')_{c'} \quad \text{(II),}$$

in which e and f both represent the number 1, g and h both represent the number 0, A and A' represent, independently of one another, a linear, bivalent $C_1$-$C_6$ alkylene group, and R7 represents a hydrogen atom, a methyl group, a 2-hydroxyethyl group, a 2-alkenyl group, a 2-aminoethyl group, or a group of formula (III).

In a further preferred embodiment, a method is characterized in that agent (a) contains at least one organic silicon compound (a2) of the formula (II), wherein e and f both represent the number 1, g and h both represent the number 0, A and A' represent, independently of one another, a methylene group ($—CH_2—$), an ethylene group ($—CH_2—CH_2—$), or a propylene group ($—CH_2—CH_2—CH_2$), and R7 represents a hydrogen atom, a methyl group, a 2-hydroxyethyl group, a 2-alkenyl group, a 2-aminoethyl group, or a group of formula (III).

To achieve the object according to the invention, suitable organic silicon compounds of formula (II) are:

3-(trimethoxysilyl)-N-[3-(trimethoxysilyl)propyl]-1-propanamine

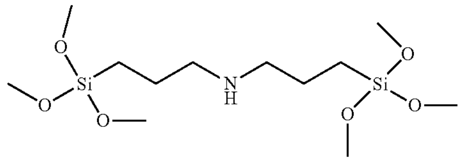

3-(triethoxysilyl)-N-[3-(triethoxysilyl)propyl]-1-propanamine

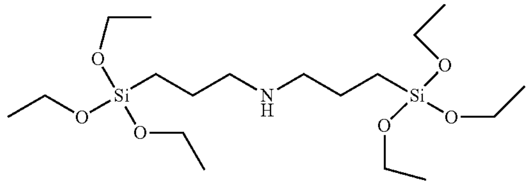 [SMILES: CCO[Si](CCCNCCC[Si](OCC)(OCC)OCC)(OCC)OCC]

N-methyl-3-(trimethoxysilyl)-N-[3-(trimethoxysilyl)propyl]-1-propanamine

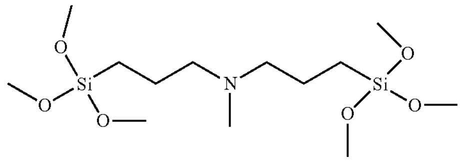

N-methyl-3-(triethoxysilyl)-N-[3-(triethoxysilyl)propyl]-1-propanamine

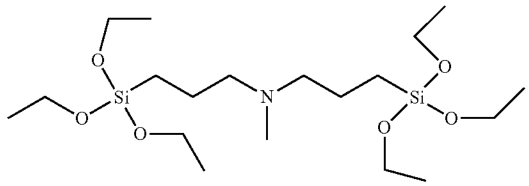

2-[bis[3-(trimethoxysilyl)propyl]amino]-ethanol

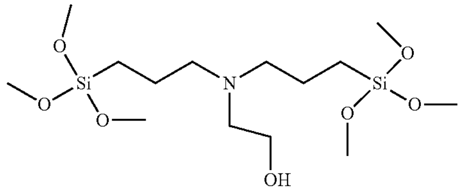

2-[bis[3-(triethoxysilyl)propyl]amino]-ethanol

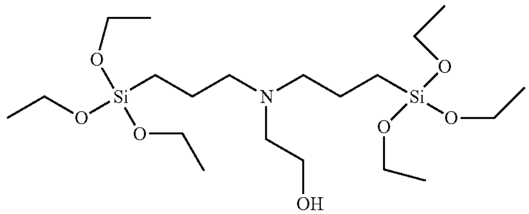 [SMILES: CCO[Si](CCCN(CCO)CCC[Si](OCC)(OCC)OCC)(OCC)OCC]

3-(trimethoxysilyl)-N,N-bis[3-(trimethoxysilyl)propyl]-1-propanamine

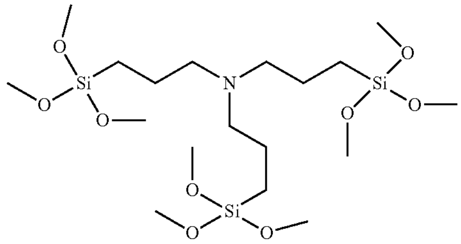

3-(triethoxysilyl)-N,N-bis[3-(triethoxysilyl)propyl]-1-propanamine

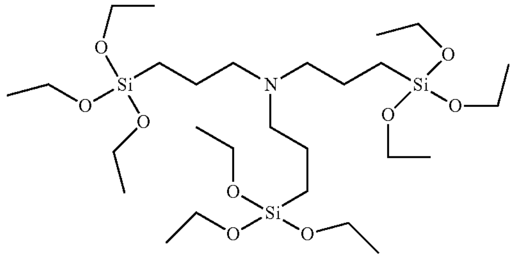 [SMILES: CCO[Si](CCCN(CCC[Si](OCC)(OCC)OCC)CCC[Si](OCC)(OCC)OCC)(OCC)OCC]

N1,N1-bis[3-(trimethoxysilyl)propyl]-1,2-ethanediamine,

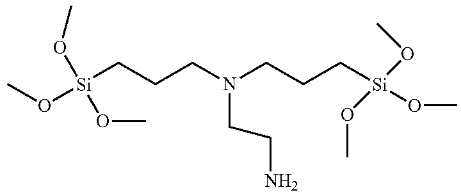

N1,N1-bis[3-(triethoxysilyl)propyl]-1,2-ethanediamine,

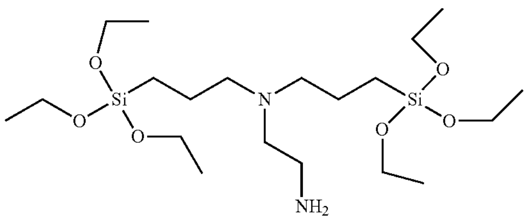 [SMILES: CCO[Si](CCCN(CCN)CCC[Si](OCC)(OCC)OCC)(OCC)OCC]

N,N-bis[3-(trimethoxysilyl)propyl]-2-propene-1-amine

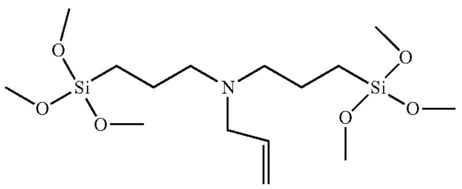

N,N-bis[3-(triethoxysilyl)propyl]-2-propene-1-amine

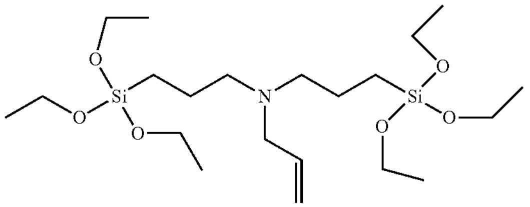 [SMILES: C=CCN(CCC[Si](OCC)(OCC)OCC)CCC[Si](OCC)(OCC)OCC]

The aforementioned organosilicon compounds of formula (II) are commercially available.

Bis(trimethoxysilylpropyl)amine with the CAS number 82985-35-1 can, for example, be purchased from Sigma-Aldrich.

Bis[3-(triethoxysilyl)propyl]amine with the CAS number 13497-18-2 can, for example, be purchased from Sigma-Aldrich.

N-methyl-3-(trimethoxysilyl)-N-[3-(trimethoxysilyl)propyl]-1-propanamine is alternatively also referred to as bis (3-trimethoxysilylpropyl)-N-methylamine and can, for example, be purchased from Sigma-Aldrich or Fluorochem.

3-(triethoxysilyl)-N,N-bis[3-(triethoxysilyl)propyl]-1-propanamine with the CAS number 18784-74-2 can, for example, be purchased from Fluorochem or Sigma-Aldrich.

In a further preferred embodiment, a method is characterized in that agent (a) contains at least one organic silicon compound (a2), which is selected from the group consisting of 3-(trimethoxysilyl)-N-[3-(trimethoxysilyl)propyl]-1-propanamine, 3-(triethoxysilyl)-N-[3-(triethoxysilyl)propyl]-1-propanamine, N-methyl-3-(trimethoxysilyl)-N-[3-(trimethoxysilyl)propyl]-1-propanamine, N-methyl-3-(triethoxysilyl)-N-[3-(triethoxysilyl)propyl]-1-propanamine, 2-[bis[3-(trimethoxysilyl)propyl]amino]-ethanol, 2-[bis[3-(triethoxysilyl)propyl]amino]-ethanol, 3-(trimethoxysilyl)-N,N-bis[3-(trimethoxysilyl)propyl]-1-propanamine, 3-(triethoxysilyl)-N,N-bis[3-(triethoxysilyl)propyl]-1-propanamine, N1,N1-bis[3-(trimethoxysilyl)propyl]-1,2-ethanediamine, N1,N1-bis[3-(triethoxysilyl)propyl]-1,2-ethanediamine, N,N-bis[3-(trimethoxysilyl)propyl]-2-propene-1-amine, and/or N,N-bis[3-(triethoxysilyl)propyl]-2-propene-1-amine.

In further dyeing tests, it has also been found to be very particularly advantageous if the agent (a) applied in the method on the keratinous material contains at least one organic silicon compound (a2) of formula (IV)

$$R_9Si(OR_{10})_k(R_{11})_m \quad (IV).$$

The compounds of formula (IV) are organosilicon compounds selected from silanes with one, two, or three silicon atoms, wherein the organosilicon compound comprises one or more hydroxyl groups and/or hydrolyzable groups per molecule.

The organic silicon compound(s) of formula (IV) can also be referred to as silanes of the alkyl alkoxysilanes type or the alkyl hydroxysilanes type, $$R_9Si(OR_{10})_k(R_{11})_m \quad (IV),$$

in which $R_9$ represents a $C_1$-$C_{18}$ alkyl group, $R_{10}$ represents a hydrogen atom or a $C_1$-$C_6$ alkyl group, $R_{11}$ represents a $C_1$-$C_6$ alkyl group, k represents an integer from 1 to 3, and m represents the integer 3-k.

In a further preferred embodiment, a method according to the invention is characterized in that the agent (a) contains at least one first organic silicon compound (a2) of the formula (IV), $$R_9Si(OR_{10})_k(R_{11})_m \quad (IV),$$

in which $R_9$ represents a $C_1$-$C_{18}$ alkyl group, $R_{10}$ represents a hydrogen atom or a $C_1$-$C_6$ alkyl group, $R_{11}$ represents a $C_1$-$C_6$ alkyl group, k represents an integer from 1 to 3, and m represents the integer 3-k.

In a further very particularly preferred embodiment, a method according to the invention is characterized in that the agent (a) contains, in addition to the organic silicon compound(s), at least one first organic silicon compound of the formula (IV), $$R_9Si(OR_{10})_k(R_{11})_m \quad (IV)$$

in which $R_9$ represents a $C_1$-$C_{18}$ alkyl group, $R_{10}$ represents a hydrogen atom or a $C_1$-$C_6$ alkyl group, $R_{11}$ represents a $C_1$-$C_6$ alkyl group, k represents an integer from 1 to 3, and m represents the integer 3-k.

In a further preferred embodiment, a method is characterized in that the agent (a) contains, in addition to the organic silicon compound(s) of formula (II), at least one further organic silicon compound of the formula (IV), $$R_9Si(OR_{10})_k(R_{11})_m \quad (IV),$$

in which $R_9$ represents a $C_1$-$C_{18}$ alkyl group, $R_{10}$ represents a hydrogen atom or a $C_1$-$C_6$ alkyl group, $R_{11}$ represents a $C_1$-$C_6$ alkyl group, k represents an integer from 1 to 3, and m represents the integer 3-k.

In a further preferred embodiment, a method is characterized in that the agent (a) contains, in addition to the organic silicon compound(s) of formula (I) and/or (II), at least one further organic silicon compound of the formula (IV), $$R_9Si(OR_{10})_k(R_{11})_m \quad (IV),$$

in which $R_9$ represents a $C_1$-$C_{18}$ alkyl group, $R_{10}$ represents a hydrogen atom or a $C_1$-$C_6$ alkyl group, $R_{11}$ represents a $C_1$-$C_6$ alkyl group, k represents an integer from 1 to 3, and m represents the integer 3-k.

In the organic silicon compounds of formula (IV), the function group $R_9$ represents a $C_1$-$C_{18}$ alkyl group. This $C_1$-$C_{18}$ alkyl group is saturated and can be linear or branched. Preferably $R_9$ represents a linear $C_1$-$C_{18}$ alkyl group. Preferably, $R_9$ represents a methyl group, an ethyl group, an n-propyl group, an n-butyl group, an n-pentyl group, an n-hexyl group, an n-octyl group, an n-dodecyl group, or an n-octadecyl group. Particularly preferably, $R_9$ represents a methyl group, an ethyl group, an n-hexyl group, or an n-octyl group.

In the organic silicon compounds of formula (IV), the functional group $R_{10}$ represents a hydrogen atom or a $C_1$-$C_6$ alkyl group. Particularly preferably, $R_{10}$ represents a methyl group or an ethyl group.

In the organic silicon compounds of formula (IV), the functional group $R_{11}$ represents a $C_1$-$C_6$ alkyl group. Particularly preferably, $R_{11}$ represents a methyl group or an ethyl group.

Furthermore, k represents an integer from 1 to 3, and m represents an integer 3-k. If k represents the number 3, then m is equal to 0. If k represents the number 2, then m is equal to 1. If k represents the number 1, then m is equal to 2.

It was possible to obtain especially stable films, i.e., dyes having the best wash-fastness, when, in the method, an agent (a) was used containing at least one organic silicon compound (a1) of formula (IV) in which the functional group k represents the number 3. In this case, the functional group m represents the number 0.

To achieve the object according to the invention, particularly well-suited organic silicon compounds of formula (IV) are:

methyltrimethoxysilane,

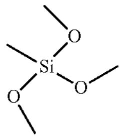

methyltriethoxysilane,

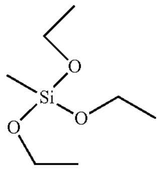

ethyltrimethoxysilane,

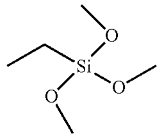

ethyltriethoxysilane,

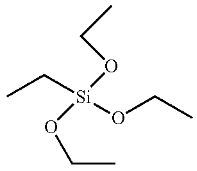

n-hexyltrimethoxysilane,

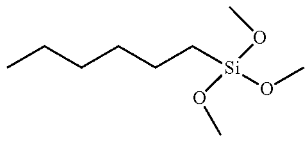

n-hexyltriethoxysilane,

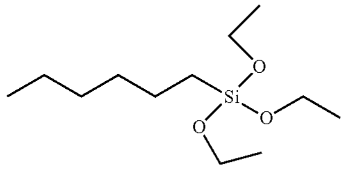 [SMILES: CCCCCC[Si](OCC)(OCC)OCC]

n-octyltrimethoxysilane,

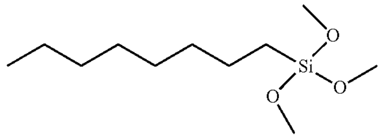

n-octyltriethoxysilane,

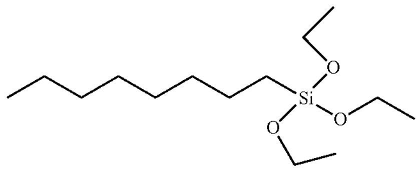 [SMILES: CCCCCCCC[Si](OCC)(OCC)OCC]

n-dodecyltrimethoxysilane, and/or

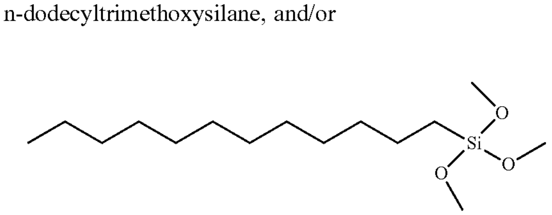

n-dodecyltriethoxysilane,

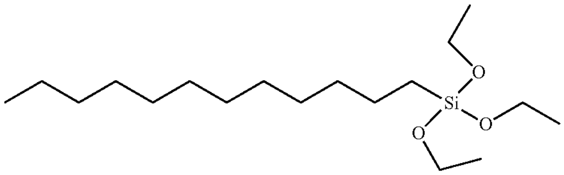 [SMILES: CCCCCCCCCCCC[Si](OCC)(OCC)OCC]

n-octadecyltrimethoxysilane, and/or n-octadecyltriethoxysilane.

In a further preferred embodiment, a method according to the invention is characterized in that the agent (a) contains at least one organic silicon compound (a2) of formula (IV), which is selected from the group consisting of
methyltrimethoxysilane,
methyltriethoxysilane,
ethyltrimethoxysilane,
ethyltriethoxysilane,
propyltrimethoxysilane,
propyltriethoxysilane,
hexyltrimethoxysilane,
hexyltriethoxysilane,
octyltrimethoxysilane,
octyltriethoxysilane,
dodecyltrimethoxysilane,
dodecyltriethoxysilane,
octadecyltrimethoxysilane, and
octadecyltriethoxysilane.

The organosilicon compounds described above are reactive compounds. In this context, it has been found to be preferred if agent (a), in relation to the total weight of agent (a), contains one or more organic silicon compounds (a2) in a total amount of 0.1 to 20 wt %, preferably 1 to 15 wt %, and particularly preferably 2 to 8 wt %.

In a further preferred embodiment, a method is characterized in that agent (a), in relation to the total weight of agent (a), contains one or more organic silicon compounds (a2) in a total amount of 0.1 to 20 wt %, preferably 1 to 15 wt %, and particularly preferably 2 to 8 wt %.

In order to achieve particularly good dyeing results, it is particularly advantageous to use the organosilicon compounds of formula (I) and/or (II) in certain ranges of amounts in the agent (a). Particularly preferably, agent (a) contains, in relation to the total weight of agent (a), one or more organic silicon compounds (a2) of the formula (I) and/or (II) in a total amount of 0.1 to 10 wt %, preferably 0.5 to 5 wt %, and particularly preferably 0.5 to 3 wt %.

In a further preferred embodiment, a method is characterized in that agent (a), in relation to the total weight of agent (a), contains one or more organic silicon compounds (a2) of the formula (I) and/or (II) in a total amount of 0.1 to 10 wt %, preferably 0.5 to 5 wt %, and particularly preferably 0.5 to 3 wt %.

Furthermore, it has been found to be very particularly preferred if the organic silicon compound(s) of formula (IV) are also contained in certain quantity ranges in agent (a). Particularly preferably, agent (a) contains, in relation to the total weight of agent (a), one or more organic silicon compounds (a2) of formula (IV) in a total amount of 0.1 to 20 wt %, preferably 2 to 15 wt %, and particularly preferably 4 to 9 wt %.

In a further preferred embodiment, a method is characterized in that agent (a), in relation to the total weight of agent (a), contains one or more organic silicon compounds (a2) of formula (IV) in a total amount of 0.1 to 20 wt %, preferably 2 to 15 wt %, and particularly preferably 3.2 to 10 wt %.

In the course of the work leading to this invention, it has been found that particularly stable and uniform films could also be obtained on the keratinous material if the agent (a) contains two, structurally different from one another, organic silicon compounds.

In a further preferred embodiment, a method according to the invention is therefore characterized in that the agent (a) contains at least two, structurally different from one another, organic silicon compounds (a2).

In a preferred embodiment, a method is characterized in that an agent (a) which contains at least one organic silicon compound of formula (I) and at least one organic silicon compound of formula (IV) is applied to the keratinous material.

In an explicitly very particularly preferred embodiment, a method is characterized in that an agent (a) which contains at least one organic silicon compounds of formula (I) and is selected from the group consisting of 3-aminopropyl)triethoxysilane and (3-aminopropyl)trimethoxysilane, and additionally comprises at least one organic silicon compound of formula (IV) selected from the group consisting of methyltrimethoxysilane, methyltriethoxysilane, ethyltrimethoxysilane, ethyltriethoxysilane, propyltrimethoxysilane, propyltriethoxysilane, hexyltrimethoxysilane, and hexyltriethoxysilane is applied to the keratinous material.

In a further preferred embodiment, a method is characterized in that agent (a) contains, in relation to the total weight of agent (a):

0.5 to 5 wt % of at least one first organic silicon compound (a2) selected from the group consisting of (3-aminopropyl)trimethoxysilane, (3-aminopropyl)triethoxysilane, (2-aminoethyl)trimethoxysilane, (2-aminoethyl)triethoxysilane, (3-dimethylaminopropyl) trimethoxysilane, (3-dimethylaminopropyl) triethoxysilane, (2-dimethylaminoethyl) trimethoxysilane, and (2-dimethylaminoethyl) triethoxysilane, and 3.2 to 10 wt % of at least one second organic silicon compound (a2) selected from the group consisting of methyltrimethoxysilane, methyltriethoxysilane, ethyltrimethoxysilane, ethyltriethoxysilane, propyltrimethoxysilane, propyltriethoxysilane, hexyltrimethoxysilane, hexyltriethoxysilane, octyltrimethoxysilane, octyltriethoxysilane, dodecyltrimethoxysilane, dodecyltriethoxysilane, octadecyltrimethoxysilane, and octadecyltriethoxysilane.

In the context of this embodiment, agent (a) contains one or more organic silicon compounds of a first group in a total amount of 0.5 to 3 wt %. The organic silicon compounds of this first group are selected from the group consisting of (3-aminopropyl)trimethoxysilane, (3-aminopropyl)triethoxysilane, (2-aminoethyl)trimethoxysilane, (2-aminoethyl)triethoxysilane, (3-dimethylaminopropyl)trimethoxysilane, (3-dimethylaminopropyl)triethoxysilane, (2-dimethylaminoethyl)trimethoxysilane, and/or (2-dimethylaminoethyl) triethoxysilane.

In the context of this embodiment, agent (a) contains one or more organic silicon compounds of a second group in a total amount of 3.2 to 10 wt %. The organic silicon compounds of this second group are selected from the group consisting of methyltrimethoxysilane, methyltriethoxysilane, ethyltrimethoxysilane, ethyltriethoxysilane, propyltrimethoxysilane, propyltriethoxysilane, hexyltrimethoxysilane, hexyltriethoxysilane, octyltrimethoxysilane, octyltriethoxysilane, dodecyltrimethoxysilane, dodecyltriethoxysilane, octadecyltrimethoxysilane, and octadecyltriethoxysilane.

Oligomers and/or Condensation Products of the Organic Silicon Compounds (a2)

In the above-described organic silicon compounds from the group consisting of silanes having one, two, or three silicon atoms (a2), even the addition of low amounts of water leads to hydrolysis or to oligomerization and/or polymerization. The extent of the oligomerization or polymerization is dependent here upon the amount of water which comes into contact with the silanes or silanes (a2). The aim of the method according to the invention is that the formation of the colored film, i.e., the final polymerization issuing from the silanes (a2), only occurs in step (2) of the method if the agent (a) is already located on the keratinous material. Nevertheless, due to the high reactivity of the silanes (a2), an oligomerization or precondensation has already taken place before application of agent (a), and the silanes (a2) may have already been oligomerized in agent (a) or already been polymerized in small portions.

For this reason, both the silanes having one, two, or three silicon atoms (a2) and the oligomers and/or condensation products thereof may be contained in agent (a). According to the invention, therefore, the phrase, "silanes having one, two, or three silicon atoms (a2)," also comprises the hydrolysis products thereof, oligomers, and/or condensation products thereof.

Oligomers and/or condensation products of the corresponding hydrolysis, are, for example, the following compounds. In this case, the condensation products represent maximum oligomeric compounds, but not polymers.

Hydrolysis of $C_1$-$C_6$ alkoxy silane of the formula (S—I) with water (reaction scheme using the example of 3-aminopropyltriethoxysilane):

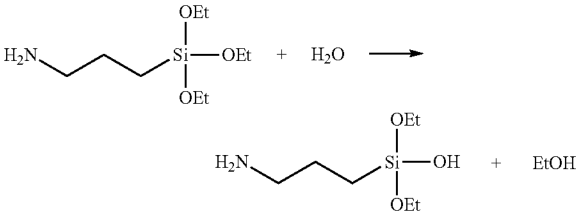

Depending upon the amount of water used, the hydrolysis reaction can also take place multiple times per $C_1$-$C_6$ alkoxy silane used:

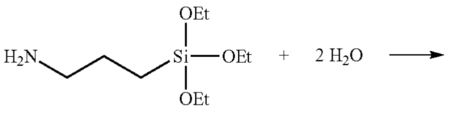

-continued

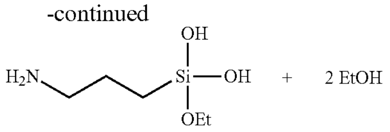

or

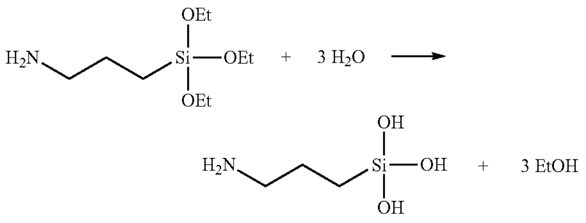

Hydrolysis of $C_1$-$C_6$ alkoxy silane of the formula (S—IV) with water (reaction scheme using the example of methyltrimethoxysilane):

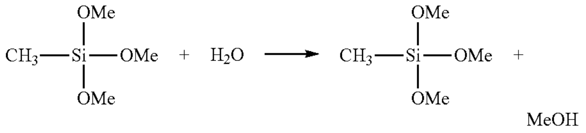

Depending upon the amount of water used, the hydrolysis reaction can also take place multiple times per $C_1$-$C_6$ alkoxy silane used:

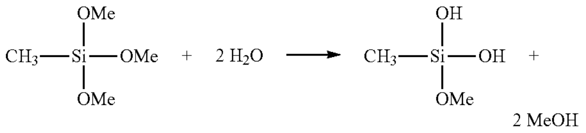

or

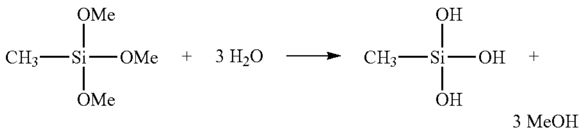

Possible condensation reactions are, for example (shown on the basis of the mixture (3-aminopropyl)triethoxysilane and methyltrimethoxysilane):

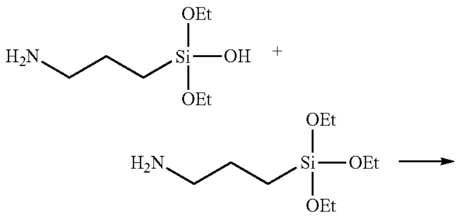

-continued

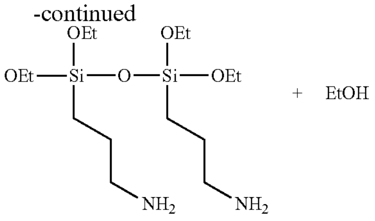

and/or

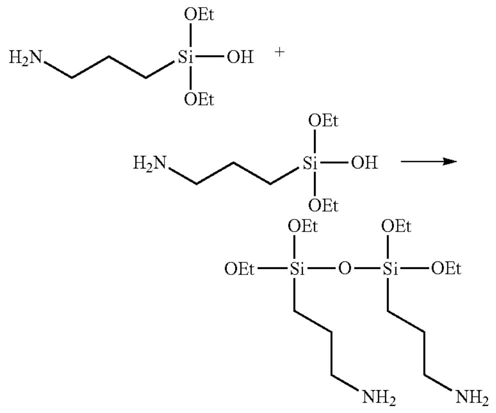

and/or

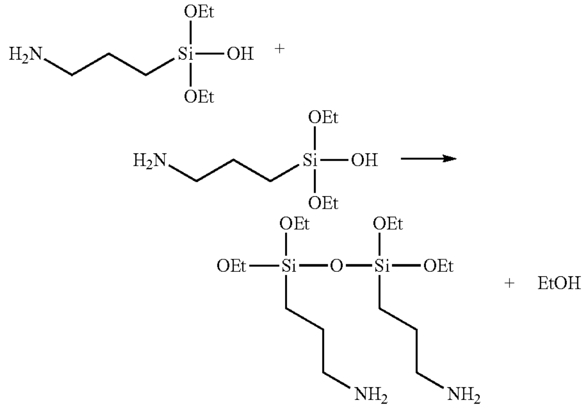

and/or

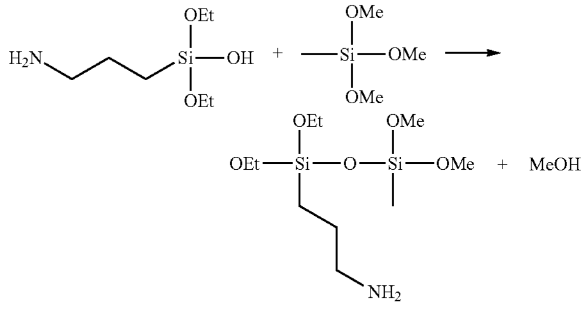

and/or

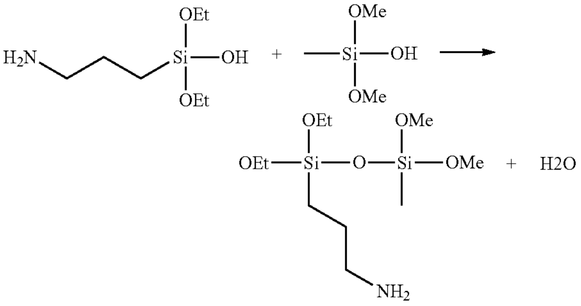

and/or

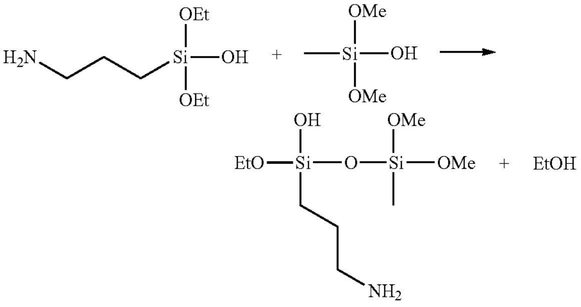

and/or

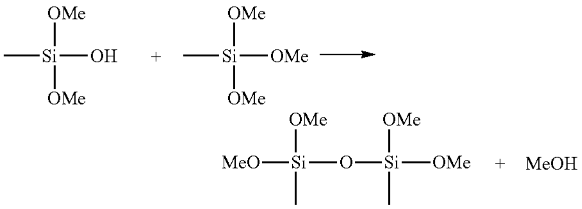

In the above reaction schemes, given by way of example, the condensation to form a dimer is shown in each case, but also further condensations to oligomers having several silane atoms are possible and also preferred.

A condensation product is understood to mean a product which is formed by reaction of at least two organic silicon compounds with at least one hydroxyl group or hydrolyzable groups per molecule, with elimination of water and/or with elimination of an alkanol. The condensation products can, for example, be dimers, but also trimers or oligomers, the condensation products being in equilibrium with the monomers. Depending upon the amount of water used or consumed in the hydrolysis, the equilibrium of monomeric organic silicon compounds to condensation product shifts.

It was possible to obtain very particularly good results when organic silicon compounds of the formula (I) and/or (II) and/or (IV) were used in the method. Because hydrolysis/condensation is already used when there are of traces of moisture, as already described above, the hydrolysis and/or condensation products of the organic silicon compounds (I) and/or (II) and/or (IV) of this embodiment are thus also included.

Chromophoric Compounds (a3) in Agent (a)

Agent (a) contains at least one chromophoric compound as a third component essential to the invention. In the formation of the film produced by the polymerization of the silanes (a2), the chromophoric compound(s) is/are stored therein and in this way is/are fixed to the keratinous surface. Such chromophoric compounds are very particularly preferably pigments and/or direct dyes, and very particularly preferably pigments.

In a further particularly preferred embodiment, a method according to the invention is characterized in that agent (a) comprises at least one chromophoric compound (a3) from the group of pigments and/or direct dyes.

In the context of a further particularly preferred embodiment, a method according to the invention is characterized in that the agent (a) contains at least one pigment (a3).

Pigments in the sense of the present invention are understood to mean chromophoric compounds which have a solubility in water, at 25° C., of less than 0.5 g/L, preferably less than 0.1 g/L, and even more preferably less than 0.05 g/L. The water solubility can be carried out, for example, by means of the method described hereinafter: 0.5 g of the pigment is weighed in a beaker. A stirring bar is added. Then, one liter of distilled water is added. This mixture is heated to 25° C. while stirring on a magnetic stirrer for one hour. If still undissolved components of the pigment are visible in the mixture after this period, the solubility of the pigment is below 0.5 g/L. If the pigment-water mixture cannot be visually assessed due to the high intensity of the pigment that may be present finely dispersed, the mixture is filtered. If a portion of undissolved pigments remains on the filter paper, the solubility of the pigment is below 0.5 g/L.

Suitable pigments may be of inorganic and/or organic origin.

In a preferred embodiment, a method is characterized in that it contains at least one chromophoric compound (a3) from the group of the inorganic and/or organic pigments.

Preferred pigments are selected from synthetic or natural inorganic pigments.

Inorganic pigments of natural origin can be produced, for example, from chalk, ocher, umbra, green earth, burnt sienna, or graphite. Furthermore, black pigments such as, for example, iron oxide black, chromatic pigments such as, for example, ultramarine or iron oxide red, and also fluorescent or phosphorescent pigments, can be used as inorganic pigments.

Colored metal oxides, hydroxides and oxide hydrates, mixed phase pigments, sulfur-containing silicates, silicates, metal sulfides, complex metal cyanides, metal sulfates, chromates, and/or molybdates are particularly suitable. Particularly preferred dye pigments are black iron oxide (CI 77499), yellow iron oxide (CI 77492), red and brown iron oxide (CI 77491), manganese violet (CI 77742), ultramarine (sodium aluminum sulfosilicates, CI 77007, Pigment Blue 29), chromium oxide hydrate (CI77289), iron blue (ferric ferrocyanide, CI77510), and/or carmine (cochineal).

Pigments which are likewise particularly preferred are colored pearlescent pigments. These are usually based upon mica and may be coated with one or more metal oxides. Mica is a phyllosilicate. The most important representatives of these silicates are muscovite, phlogopite, paragonite, biotite, lepidolite, and margarite. In order to prepare the pearlescent pigments in conjunction with metal oxides, the mica, primarily muscovite or phlogopite, is coated with a metal oxide.

Accordingly, a preferred method is characterized in that agent (a) contains at least one inorganic pigment (a3)—preferably selected from the group of colored metal oxides, metal hydroxides, metal oxide hydrates, silicates, metal sulfides, complex metal cyanides, metal sulphates, bronze pigments, and/or from mica-based colored pigments which are coated with at least one metal oxide and/or a metal oxychloride.

A preferably suitable pigment based upon synthetic mica is, for example, Timiron® SynWhite Satin from Merck.

In a further preferred embodiment, the method is characterized in that agent (a) and/or agent (b) comprises at least one chromophoric compound from the group of pigments which is selected from pigments based upon natural or synthetic mica, which are coated with one or more metal oxides from the group consisting of titanium dioxide (CI 77891), black iron oxide (CI 77499), yellow iron oxide (CI 77492), red and/or brown iron oxide (CI 77491, CI 77499), manganese violet (CI 77742), ultramarine (sodium aluminum sulfosilicates, CI 77007, Pigment Blue 29), chromium oxide hydrate (CI 77289), chromium oxide (CI 77288), and/or iron blue (ferric ferrocyanide, CI 77510).

Further suitable pigments are based upon metal-oxide-coated, plate-shaped borosilicates. These are coated, for example, with tin oxide, iron oxide(s), silicon dioxide, and/or titanium dioxide. Such borosilicate-based pigments are available, for example, under the name, MIRAGE from Eckart, or Reflecks from BASF SE.

Examples of particularly suitable color pigments are commercially available, for example, under the trade names, Rona®, Colorona®, Xirona®, Dichrona®, and Timiron® from the company Merck, Ariabek® and Unipure® from the company Sensient, Prestige® or SynCrystal from the company Eckart Cosmetic Colors, Flamenco®, Cellini®, Cloisonne®, Duocrome®, Gemtone®, Timica®, MultiReflections, Chione from the company BASF SE, and Sunshine® from the company Sunstar.

Very particularly preferred dye pigments having the trade name, Colorona®, are, for example:

Colorona Copper, Merck, MICA, CI 77491 (IRON OXIDES)

Colorona Copper Fine, Merck, MICA, CI 77491 (IRON OXIDES)

Colorona Passion Orange, Merck, mica, CI 77491 (iron oxides), alumina

Colorona Patina Silver, Merck, MICA, CI 77499 (IRON OXIDES), CI 77891 (TITANIUM DIOXIDE)

Colorona RY, Merck, CI 77891 (TITANIUM DIOXIDE), MICA, CI 75470 (CARMINE)

Colorona Oriental Beige, Merck, MICA, CI 77891 (TITANIUM DIOXIDE), CI 77491 (IRON OXIDES)

Colorona Dark Blue, Merck, MICA, TITANIUM DIOXIDE, FERRIC FERROCYANIDE

Colorona Chameleon, Merck, CI 77491 (IRON OXIDES), MICA

Colorona Aborigine Amber, Merck, MICA, CI 77499 (IRON OXIDES), CI 77891 (TITANIUM DIOXIDE)

Colorona Blackstar Blue, Merck, CI 77499 (IRON OXIDES), MICA

Colorona Patagonian Purple, Merck, MICA, CI 77491 (IRON OXIDES), CI 77891 (TITANIUM DIOXIDE), CI 77510 (FERRIC FERROCYANIDE)

Colorona Red Brown, Merck, MICA, CI 77491 (IRON OXIDES), CI 77891 (TITANIUM DIOXIDE)

Colorona Russet, Merck, CI 77491 (TITANIUM DIOXIDE), MICA, CI 77891 (IRON OXIDES)

Colorona Imperial Red, Merck, MICA, TITANIUM DIOXIDE (CI 77891), D&C RED NO. 30 (CI 73360)

- Colorona Majestic Green, Merck, CI 77891 (TITANIUM DIOXIDE), MICA, CI 77288 (CHROMIUM OXIDE GREENS)
- Colorona Light Blue, Merck, MICA, TITANIUM DIOXIDE (CI 77891), FERRIC FERROCYANIDE (CI 77510)
- Colorona Red Gold, Merck, MICA, CI 77891 (TITANIUM DIOXIDE), CI 77491 (IRON OXIDES)
- Colorona Gold Plus MP 25, Merck, MICA, TITANIUM DIOXIDE (CI 77891), IRON OXIDES (CI 77491)
- Colorona Carmine Red, Merck, MICA, TITANIUM DIOXIDE, CARMINE
- Colorona Blackstar Green, Merck, MICA, CI 77499 (IRON OXIDES)
- Colorona Bordeaux, Merck, MICA, CI 77491 (IRON OXIDES)
- Colorona Bronze, Merck, MICA, CI 77491 (IRON OXIDES)
- Colorona Bronze Fine, Merck, MICA, CI 77491 (IRON OXIDES)
- Colorona Fine Gold MP 20, Merck, MICA, CI 77891 (TITANIUM DIOXIDE), CI 77491 (IRON OXIDES)
- Colorona Sienna Fine, Merck, CI 77491 (IRON OXIDES), MICA
- Colorona Sienna, Merck, MICA, CI 77491 (IRON OXIDES)
- Colorona Precious Gold, Merck, mica, CI 77891 (titanium dioxide), silica, CI 77491 (iron oxides), tin oxide
- Colorona Sun Gold Sparkle MP 29, Merck, MICA, TITANIUM DIOXIDE, IRON OXIDES, MICA, CI 77891, CI 77491 (EU)
- Colorona Mica Black, Merck, CI 77499 (iron oxides), mica, CI 77891 (titanium dioxide)
- Colorona Bright Gold, Merck, mica, CI 77891 (titanium dioxide), CI 77491 (iron oxides)
- Colorona Blackstar Gold, Merck, MICA, CI 77499 (IRON OXIDES)
- Colorona® SynCopper, Merck, synthetic fluorphlogopite (and) iron oxides
- Colorona® SynBronze, Merck, synthetic fluorphlogopite (and) iron oxides Additional particularly preferred pigments with the trade name, Xirona®, are for example:

- Xirona® Golden Sky, Merck, silica, CI 77891 (titanium dioxide), tin oxide
- Xirona® Caribbean Blue, Merck, mica, CI 77891 (titanium dioxide), silica, tin oxide
- Xirona® Kiwi Rose, Merck, silica, CI 77891 (titanium dioxide), tin oxide
- Xirona® Magic Mauve, Merck, silica, CI 77891 (titanium dioxide), tin oxide
- Xirona® Le Rouge, Merck, iron oxides (and) silica In addition, particularly preferred pigments with the trade name, Unipure®, are, for example:

- Unipure Red LC 381 EM, Sensient CI 77491 (iron oxides), silica
- Unipure Black LC 989 EM, Sensient, CI 77499 (iron oxides), silica
- Unipure Yellow LC 182 EM, Sensient, CI 77492 (iron oxides), silica Likewise, very particularly preferred dye pigments with the trade name, Flamenco®, are, for example:

- Flamenco® Summit Turquoise T30D, BASF, titanium dioxide (and) mica
- Flamenco® Super Violet 530Z, BASF, mica (and) titanium dioxide In the context of another embodiment, the agent (a) and/or agent (b) used in the method can also contain one or more chromophoric compounds from the group of organic pigments.

The organic pigments according to the invention are correspondingly insoluble, organic dyes or color varnishes, which may be selected, for example, from the group of nitroso, nitro, azo, xanthene, anthraquinone, isoindolinone, isoindoline, quinacridone, perinone, perylene, diketopyrrolopyrrole, indigo, thioindido, dioxazine, and/or triarylmethane compounds.

Particularly well suited organic pigments can for example include carmine, quinacridone, phthalocyanine, sorghum, blue pigments with the Color Index numbers CI 42090, CI 69800, CI 69825, CI 73000, CI 74100, CI 74160, yellow pigments with the Color Index numbers CI 11680, CI 11710, CI 15985, CI 19140, CI 20040, CI 21100, CI 21108, CI 47000, CI 47005, green pigments with the Color Index numbers CI 61565, CI 61570, CI 74260, orange pigments with the Color Index numbers CI 11725, CI 15510, CI 45370, CI 71105, red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915, and/or CI 75470.

In another particularly preferred embodiment of a method according to the invention, agent (a) contains at least one organic pigment (a3), which is preferably selected from the group consisting of carmine, quinacridone, phthalocyanine, sorghum, blue pigments with the Color Index numbers CI 42090, CI 69800, CI 69825, CI 73000, CI 74100, CI 74160, yellow pigments with the Color Index numbers CI 1 1680, CI 11710, CI 15985, CI 19140, CI 20040, CI 21100, CI 21 108, CI 47000, CI 47005, green pigments with the Color Index numbers CI 61565, CI 61570, CI 74260, orange pigments with the Color Index numbers CI 11725, CI 15510, CI 45370, CI 71105, red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915, and CI 75470.

The organic pigment can furthermore also be a color varnish. The term, color varnish, is understood, within the meaning of the invention, to mean particles which comprise a layer of absorbed dyes, the unit consisting of particle and dye being insoluble under the above-mentioned conditions. The particles may, for example, be inorganic substrates, which may be aluminum, silica, calcium borosilicate, calcium aluminum borosilicate, or aluminum.

For example, the Alizarin color varnish can be used as color varnish.

For the dyeing of the keratinous material, pigments of a specific shape may also have been used. For example, a pigment based upon a lamellar and/or lenticular, small substrate plate may be used. Furthermore, the dyeing is also possible based upon a small substrate plate which comprises a vacuum-metalized pigment.

In the context of another embodiment, a method according to the invention can be characterized in that agent (a) also contains one or more chromophoric compounds (a3) from the group of pigments based upon a lamellar substrate plate, pigments based upon a lenticular substrate plate, and vacuum-metalized pigments.

The substrate plates of this type have a mean thickness of at most 50 nm, preferably less than 30 nm, and particularly preferably at most 25 nm—for example, at most 20 nm. The mean thickness of the substrate plates is at least 1 nm, preferably at least 2.5 nm, and especially preferably 5 nm—for example, at least 10 nm. Preferred ranges for the thickness of the substrate plates are 2.5 to 50 nm, 5 to 50 nm, 10 to 50 nm; 2.5 to 30 nm, 5 to 30 nm, 10 to 30 nm; 2.5 to 25 nm, 5 to 25 nm, 10 to 25 nm, 2.5 to 20 nm, 5 to 20 nm, and 10 to 20 nm. Preferably, each small substrate plate has as uniform a thickness as possible.

Due to the small thickness of the small substrate plates, the pigment has a particularly high covering capacity.

The substrate plates preferably have a monolithic structure. Monolithic means, in this context, consisting of a single closed unit without fractures, layers or inclusions, it being possible, however, for structural changes to occur within the small substrate plates. The small substrate plates are preferably constructed homogeneously, i.e., no concentration gradient occurs within the small plates. In particular, the small substrate plates are not constructed in layers and have no particles distributed therein.

The size of the small substrate plate can be matched to the respective application, and in particular to the desired effect on the keratin material. As a rule, the substrate plates have a mean maximum diameter of approximately 2 to 200 μm, and in particular approximately 5 to 100 μm.

In a preferred embodiment, the form factor (aspect ratio), expressed by the ratio of the mean size to the mean thickness, is at least 80, preferably at least 200, more preferably at least 500, and particularly preferably more than 750. The mean size of the uncoated substrate plates is understood to mean the d50 value of the uncoated substrate plate. Unless stated otherwise, the d50 value was determined using a device of the Sympatec Helos type with QUIXEL wet dispersion. To prepare the sample, the sample to be investigated was pre-dispersed in isopropanol for a period of 3 minutes.

The small substrate plates may be constructed from any material that can be made into the form of a small plate.

They can be of natural origin, but can also be produced synthetically. Materials from which the small substrate plates can be constructed are, for example, metals and metal alloys, metal oxides, preferably aluminum oxide, inorganic compounds, and minerals such as mica and (semi-) precious stones, as well as plastics. Preferably, the substrate plates are made of metal (alloy) s.

Any metal suitable for metallic pearlescent pigments is possible as the metal. Such metals are, inter alia, iron and steel, and all air-resistant and water-resistant (semi-) metals such as, for example, platinum, zinc, chromium, molybdenum, and silicon, as well as alloys thereof such as aluminum bronzes and brass. Preferred metals are aluminum, copper, silver, and gold.

Preferred small substrate plates are small aluminum plates and small brass plates, small substrate plates made of aluminum being particularly preferred.

Lamellar small substrate plates are characterized by an irregularly structured edge, and are also referred to as "cornflakes" due to their appearance.

Due to their irregular structure, pigments based upon lamellar, small substrate plates produce a high fraction of scattered light. In addition, the pigments based upon lamellar, small substrate plates do not completely cover the existing color of a keratin material, and, for example, effects can be achieved analogous to a natural graying.

Lenticular (=lens-shaped), small substrate plates have a substantially regular round edge and are also referred to as "silver dollars" due to their appearance. Due to their regular structure, the fraction of the reflected light predominates in the case of pigments based upon lenticular, small substrate plates.

Vacuum-metalized pigments (VMP) can be obtained, for example, by releasing metals, metal alloys, or metal oxides from correspondingly coated films. These are characterized by a particularly small thickness of the substrate plates in the range of 5 to 50 nm and by a particularly smooth surface having increased reflectivity. Small substrate plates which comprise a vacuum-metalized pigment are also referred to, in the context of this application, as VMP small substrate plates. VMP small substrate plates made of aluminum can be obtained, for example, by releasing aluminum from metalized films.

The small substrate plates made of metal or metal alloy can be passivated—for example, by anodizing (oxide layer) or chromatizing.

Uncoated lamellar, lenticular, and/or VPM substrate plates, and in particular those made of metal or metal alloy, reflect the incident light to a high degree and produce a light-dark flop. These have proven to be particularly preferred for use in agent (a).

Suitable pigments based upon a lamellar small substrate plate include, for example, the pigments of the VISIONAIRE series by Eckart.

Pigments based upon a lenticular, small substrate plate are available, for example, under the name, Alegrace® Gorgeous, from the company Schlenk Metallic Pigments GmbH.

Pigments based upon a small substrate plate, which comprises a vacuum-metalized pigment, are available, for example, under the names, Alegrace® Marvelous or Alegrace® Aurous, from the company Schlenk Metallic Pigments GmbH.

Within the context of a further embodiment, a method according to the invention is characterized in that the agent (a) contains, in relation to the total weight of the agent (a), one or more pigments in a total amount of 0.001 to 20 wt %, and in particular 0.05 to 5 wt %.

The agents (a) used in the method can also contain one or more direct dyes as chromophoric compound(s). Direct dyes are dyes which attach directly to the hair and do not require an oxidative process to form the color. Direct dyes are usually nitrophenylenediamines, nitroaminophenols, azo dyes, anthraquinones, triarylmethane dyes, or indophenols.

The direct dyes in the sense of the present invention have a solubility in water (760 mmHg) at 25° C. of more than 0.5 g/L and are therefore not to be regarded as pigments. In the sense of the present invention, the direct dyes preferably have a solubility in water (760 mmHg) at 25° C. of more than 1 g/L.

Direct dyes can be divided into anionic, cationic, and non-ionic direct dyes.

In a further preferred embodiment, the method is characterized in that the agent (a) contains as a chromophoric compound (a3) at least one anionic, cationic, and/or non-ionic direct dye.

Preferred cationic direct dyes are Basic Blue 7, Basic Blue 26, Basic Violet 2 and Basic Violet 14, Basic Yellow 57, Basic Red 76, Basic Blue 16, Basic Blue 347 (Cationic Blue 347/Dystar), HC Blue No. 16, Basic Blue 99, Basic Brown 16, Basic Brown 17, Basic Yellow 57, Basic Yellow 87, Basic Orange 31, Basic Red 51, and Basic Red 76.

In particular, non-ionic nitro dyes and quinone dyes and neutral azo dyes, for example, can be used as non-ionic direct dyes. Suitable non-ionic direct dyes are the compounds known under the international designations or trade names, HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, as well as 1,4-diamino-2-nitrobenzene, 2-amino-4-nitrophenol, 1,4-bis-(2-hydroxyethyl)-amino-2-nitrobenzene, 3-nitro-4-(2-hydroxyethyl)-aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)-amino-5-chloro-2-nitrobenzene, 4-amino-3-nitrophenol, 1-(2'-ureidoethyl)amino-4-nitrobenzene, 2-[(4-amino-2-nitrophenyl)amino]-benzoic acid, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid, and 2-chloro-6-ethylamino-4-nitrophenol.

Anionic direct dyes are also referred to as acid dyes. Acid dyes are understood to be direct dyes that have at least one carboxylic acid group (—COOH) and/or a sulfonic acid group (—$SO_3H$). Depending upon the pH, the protonated forms (—COOH, —$SO_3H$) of carboxylic acid or sulfonic acid groupings are present in equilibrium with their deprotonated forms (—$COO^-$, —$SO_3^-$). The proportion of the protonated forms increases with decreasing pH. If direct dyes are used in the form of their salts, the carboxylic acid groups or sulfonic acid groups are thus present in the deprotonated form and are neutralized to maintain the electro-neutrality with corresponding stoichiometric equivalents of cations. The acid dyes can also be used in the form of their sodium salts and/or their potassium salts.

The acid dyes within the meaning of the present invention have a solubility in water (760 mmHg) at 25° C. of more than 0.5 g/L and are therefore not to be regarded as pigments. Within the meaning of the present invention, the acid dyes preferably have a solubility in water (760 mmHg) at 25° C. of more than 1 g/L.

The alkaline earth salts (for example, calcium salts and magnesium salts) or aluminum salts of acid dyes often have poorer solubility than the corresponding alkali salts. If the solubility of these salts is below 0.5 g/L (25° C., 760 mmHg), they do not fall under the definition of a direct dye.

An essential feature of the acid dyes is their ability to form anionic charges, wherein the carboxylic acid groups or sulfonic acid groups responsible for this are usually linked to different chromophoric systems. Suitable chromophoric systems are found, for example, in the structures of nitrophenylenediamines, nitroaminophenols, azo dyes, anthraquinone dyes, triarylmethane dyes, xanthene dyes, rhodamine dyes, oxazine dyes, and/or indophenol dyes.

For example, one or more compounds from the following group can be selected as suitable acid dyes: Acid Yellow 1 (D&C Yellow 7, Citronin A, Ext. D&C Yellow No. 7, Japan Yellow 403, CI 10316, COLIPA no B001), Acid Yellow 3 (COLIPA no: C 54, D&C Yellow No 10, Quinoline Yellow, E104, Food Yellow 13), Acid Yellow 9 (CI 13015), Acid Yellow 17 (CI 18965), Acid Yellow 23 (COLIPA no C 29, Covacap Jaune W 1 100 (LCW), Sicovit Tartrazine 85 E 102 (BASF), Tartrazine, Food Yellow 4, Japan Yellow 4, FD&C Yellow No. 5), Acid Yellow 36 (CI 13065), Acid Yellow 121 (CI 18690), Acid Orange 6 (CI 14270), Acid Orange 7 (2-Naphthol orange, Orange II, $C_1$ 15510, D&C Orange 4, COLIPA no C015), Acid Orange 10 (C.I. 16230; Orange G sodium salt), Acid Orange 11 (CI 45370), Acid Orange 15 (CI 50120), Acid Orange 20 (CI 14600), Acid Orange 24 (BROWN 1; CI 20170; KATSU201; nosodiumsalt; Brown No. 201; RESORCIN BROWN; ACID ORANGE 24; Japan Brown 201; D & C Brown No. 1), Acid Red 14 (C.I. 14720), Acid Red 18 (E124, Red 18; CI 16255), Acid Red 27 (E 123, CI 16185, C-Rot 46, Echtrot D, FD&C Red No. 2, Food Red 9, Naphtholrot S), Acid Red 33 (Red 33, Fuchsia Red, D&C Red 33, CI 17200), Acid Red 35 (CI C.I. 18065), Acid Red 51 (CI 45430, Pyrosin B, Tetraiodfluorescein, Eosin J, Iodeosin), Acid Red 52 (CI 45100, Food Red 106, Solar Rhodamine B, Acid Rhodamine B, Red no 106 Pontacyl Brilliant Pink), Acid Red 73 (CI CI 27290), Acid Red 87 (Eosin, CI 45380), Acid Red 92 (COLIPA no C53, CI 45410), Acid Red 95 (CI 45425, Erythtosine. Simacid Erythrosine Y), Acid Red 184 (CI 15685), Acid Red 195, Acid Violet 43 (Jarocol Violet 43, Ext. D&C Violet no 2, C.I. 60730, COLIPA no C063), Acid Violet 49 (CI 42640), Acid Violet 50 (CI 50325), Acid Blue 1 (Patent Blue, CI 42045), Acid Blue 3 (Patent Blau V, CI 42051), Acid Blue 7 (CI 42080), Acid Blue 104 (CI 42735), Acid Blue 9 (E 133, Patentblau A E, Amidoblau A E, Erioglaucin A, CI 42090, C.I. Food Blue 2), Acid Blue 62 (CI 62045), Acid Blue 74 (E 132, CI 73015), Acid Blue 80 (CI 61585), Acid Green 3 (CI 42085, FoodgreenI), Acid Green 5 (CI 42095), Acid Green 9 (C.1.42100), Acid Green 22 (C.1.42170), Acid Green 25 (CI 61570, Japan Green 201, D&C Green No. 5), Acid Green 50 (Brilliant Acid Green BS, C.I. 44090, Acid Brilliant Green BS, E 142), Acid Black 1 (Black no 401, Naphthalene Black 10B, Amido Black 10B, CI 20 470, COLIPA no B15), Acid Black 52 (CI 15711), Food Yellow 8 (CI 14270), Food Blue 5, D&C Yellow 8, D&C Green 5, D&C Orange 10, D&C Orange 11, D&C Red 21, D&C Red 27, D&C Red 33, D&C Violet 2, and/or D&C Brown 1.

The water solubility of the anionic direct dyes can be determined, for example, in the following manner. 0.1 g of the anionic direct dye is placed in a beaker. A stirring bar is added. Then 100 ml of water added. This mixture is heated to 25° C. on a magnetic stirrer. The mixture is stirred for 60 minutes. Thereafter, the aqueous mixture is visually assessed. If there are still undissolved residues, the amount of water is increased—for example, in steps of 10 mL. Water is added until the amount of dye used has dissolved completely. If the dye-water mixture cannot be visually assessed due to the high intensity of the dye, the mixture is filtered. If a proportion of undissolved dyes remains on the filter paper, the solubility test is repeated with a larger amount of water. If the 0.1 g of the anionic direct dye dissolves at 25° C. in 100 ml of water, the solubility of the dye is 1 g/L.

Acid yellow 1 bears the names, 8-hydroxy-5,7-dinitro-2-naphthalenesulfonic acid disodium and has a solubility in water of at least 40 g/L (25° C.).

Acid Yellow 3 is a mixture of the sodium salts of mono- and disulfonic acids of 2-(2-quinolyl)-1H-indene-1,3 (2H) dione and has a water solubility of 20 g/L (25° C.).

Acid Yellow 9 is the disodium salt of 8-hydroxy-5,7-dinitro-2-naphthalenesulfonic acid; its water solubility is over 40 g/L (25° C.).

Acid Yellow 23 is the trisodium salt of 4,5-dihydro-5-oxo-1-(4-sulfophenyl)-4-((4-sulfophenyl)azo)-1H-pyrazole-3-carboxylic acid and is readily soluble in water at 25° C.

Acid Orange 7 is the sodium salt of 4-[(2-hydroxy-1-naphthyl) azo]benzene sulfonate. Its water solubility is more than 7 g/L (25° C.).

Acid Red 18 is the trisodium salt of 7-hydroxy-8-[(E)-(4-sulfonato-1-naphthyl)-diazenyl)]-1,3-naphthalenedisulfonate and has a very high water solubility of more than 20 wt %.

Acid Red 33 is the disodium salt of 5-amino4-hydroxy-3-(phenylazo)-naphthalene2,7-disulfonate; its water solubility is 2.5 g/L (25° C.).

Acid Red 92 is the disodium salt of 3,4,5,6-tetrachloro-2-(1,4,5,8-tetrabromo-6-hydroxy-3-oxoxanthene-9-yl)benzoic acid, the water solubility of which is greater than 10 g/L (25° C.).

Acid Blue 9 is the disodium salt 2-({4-[N-ethyl(3-sulfonatobenzyl]amino]phenyl}-{4-[(N-ethyl(3-sulfonato-benzyl)imino]-2,5-cyclohexadien-1-ylidene}methyl)-benzenesulfonate and has a water solubility of more than 20 wt % (25° C.).

The direct dye or dyes, and in particular the anionic direct dyes, can be used in various amounts in agent (a), depending upon the desired color intensity. Good results could be obtained if agent (a), in relation to the total weight of agent (a), contains one or more direct dyes (a3) in a total amount of 0.01 to 10 wt %, preferably of 0.1 to 8 wt %, further preferably of 0.2 to 6 wt %, and very particularly preferably of 0.5 to 4.5 wt %.

Cosmetic Carrier (a4) in Agent (a)

The agent (a) contains the organic silanes (a2) and the chromophoric compounds (a3) particularly preferably in a cosmetic carrier. Because agent (a) is also water-poor or anhydrous, this cosmetic carrier is not water. Particularly suitable cosmetic carriers are, for example, the compounds from the group of poly-$C_1$-$C_6$ alkylene glycols, 1,2-propylene glycol, 1,3-propylene glycol, 1,2-butylene glycol, dipropylene-glycol, ethanol, isopropanol, diethylene glycol monoethyl ether, glycerol, phenoxyethanol, and benzyl alcohol. Poly-$C_1$-$C_6$ alkylene glycols, and in particular polyethylene glycols, have a very particularly good suitability here.

Within the scope of a further particularly preferred embodiment, a method according to the invention is characterized in that agent (a) contains at least one cosmetic carrier (a4) from the group consisting of poly-$C_1$-$C_6$ alkylene glycols, 1,2-propylene glycol, 1,3-propylene glycol, 1,2-butylene glycol, dipropylene glycol, ethanol, isopropanol, diethylene glycol monoethyl ether, glycerol, phenoxyethanol and benzyl alcohol, and very particularly preferably of polyethylene glycols.

Alternatively, 1,2-propylene glycol is also used as 1,2-propanediol, and bears the CAS numbers 57-55-6[(RS)-1,2dihydroxypropane], 4254-14-2 [(R)-1,2dihydroxypropane], and 4254-153[(S)-1,2dihydroxypropane]. Ethylene glycol is alternatively also referred to as 1,2-ethanediol and bears the CAS number 107-21-1. Glycerol is alternatively also referred to as 1,2,3-propanetriol and bears the CAS number 56-81-5. Phenoxyethanol has the CAS number 122-99-6.

All the solvents described above are commercially available from various chemicals suppliers such as Aldrich or Fluka.

A very particularly suitable solution is alkylene glycols of the formula (AG)

$$H{-}O{-}\left[CH_2{-}CH_2{-}O\right]_x{-}H, \qquad \text{(AG)}$$

in which x represents an integer from 1 to 10,000, preferably an integer from 2 to 800, further preferably an integer from 3 to 600, even more preferably an integer from 3 to 400, and very particularly preferably an integer from 4 to 200, In the context of a further very particularly preferred embodiment, a method according to the invention is therefore characterized in that agent (a) contains one or more alkylene glycols (a4) of the formula (AG), $$H{-}O{-}\left[CH_2{-}CH_2{-}O\right]_x{-}H, \qquad \text{(AG)}$$

in which x represents an integer from 1 to 10,000, preferably an integer from 2 to 800, further preferably an integer from 3 to 600, even more preferably an integer from 3 to 400, and very particularly preferably an integer from 4 to 200.

The alkylene glycols of the formula (AG) are protic substances having at least one hydroxy group which, based upon their repeat unit —CH2-CH2-O—, if x represents a value of at least 2, can also be referred to as polyalkylene glycols or polyethylene glycols. In the alkylene glycols of the formula (AG), x represents an integer of 1 to 10,000. In the context of the work leading to this invention, it has been found that these polyethylene glycols exhibit particularly good suitability, on the one hand, to improve the fastness properties of the coloring agents and, on the other, also to optimally adjust the viscosity of the agents.

Depending upon their chain length, polyethylene glycols are liquid or solid water-soluble polymers. Polyethylene glycols with a molecular mass between 200 g/mol and 400 g/mol are non-volatile liquids at room temperature. PEG 600 has a melting range of 17 to 22° C. and thus a pasty consistency. With molecular masses over 3,000 g/mol, the PEG are solid substances and are marketed as flakes or powders.

Above all, the use of low molecular weight alkylene glycols (or polyethylene glycols) has proven to be well suited to achieving the object according to the invention. In the case of low molecular weight alkylene glycols (or polyethylene glycols), in the sense of the present invention, x represents an integer from 1 to 100, preferably an integer from 1 to 80, further preferably an integer from 2 to 60, even more preferably an integer from 3 to 40, even more preferably an integer from 4 to 20, and very particularly preferably an integer from 6 to 15.

In a further very particularly preferred embodiment, an agent according to the invention is characterized in that it comprises at least one alkylene glycol (a4) of the formula (AG-1), $$HO{-}\left[CH_2{-}CH_2{-}O\right]_{x1}{-}H, \qquad \text{(AG-1)}$$

in which x1 represents an integer from 1 to 100 preferably an integer from 1 to 80, further preferably an integer from 2 to 60, even more preferably an integer from 3 to 40, even more preferably an integer from 4 to 20, and very particularly preferably an integer from 6 to 15.

A very particularly preferred low molecular weight polyethylene glycol is, for example, PEG 8. PEG-8 comprises on average 8 ethylene glycol units (x1=8), has a mean molecular weight of 400 g/mol, and bears the CAS number 25322-68-3. PEG-8 alternatively is also known as PEG 400 and is commercially available, for example, from the company APS.

Further suitable low molecular weight polyethylene glycols are, for example, PEG-6, PEG-7, PEG-9, and PEG-10.

Another well-suited polyethylene glycol is, for example, PEG-32. PEG-32 comprises 32 ethylene glycol units (x1=32), has a mean molecular weight of 1,500 g/mol, and bears the CAS number 25322-68-3. PEG-32 alternatively is also as PEG 1500 and can be purchased commercially from Clariant, for example.

Furthermore, the use of high molecular weight polyethylene glycols has also proven to be well suited for achieving the object according to the invention.

High molecular weight polyethylene glycols in the sense of the present invention can be represented by the formula (AG-2), wherein the index number x2 represents an integer from 101 to 10,000

$$HO-\left[CH_2-CH_2-O\right]_{x2}-H. \qquad (AG-2)$$

With very particularly well-suited high molecular weight polyethylene glycols, x2 represents an integer from 101 to 1,000, preferably an integer from 105 to 800, further preferably an integer from 107 to 600, even more preferably an integer from 109 to 400, and very particularly preferably an integer from 110 to 200.

In a further very particularly preferred embodiment, an agent according to the invention is characterized in that it comprises at least one alkylene glycol (a4) of the formula (AG-2), $$HO-\left[CH_2-CH_2-O\right]_{x2}-H, \qquad (AG-2)$$

in which x2 represents an integer from 101 to 1,000, preferably an integer from 105 to 800, further preferably an integer from 107 to 600, even more preferably an integer from 109 to 400, and very particularly preferably an integer from 110 to 200.

A very particularly suitable high molecular weight polyethylene glycol is, for example, PEG 6000, which is commercially available from National Starch (China). The molecular weight of PEG 6000 is 6,000 to 7,500 g/mol, corresponding to an x2 value of 136 to 171.

Another well-suited polyethylene glycol is PEG 12000, which is sold commercially, for example, under the trade name, Polyethylene Glycol 12000 S (or PEG 12000 S) by CG Chemikalien. The molecular weight of PEG 12000 is specified as 10,500 to 15,000 g/mol, corresponding to an x2 value of 238 to 341.

Another well-suited polyethylene glycol is also PEG 20000, which can be commercially purchased under the trade name, Polyglycol 20000 P, or the alternative name, PEG-350, from Clariant. For PEG 20000, if a molecular weight of on average 20,000 g/mol, is specified, this corresponds to an x2 value of 454.

Preferably, agent (a) contains, in relation to the total weight of agent (a), the previously described cosmetic carriers (a4) in a total amount of 10.0 to 99.0 wt %, preferably of 30.0 to 99.0 wt %, further preferably of 50.0 to 99.0 wt %, and very particularly preferably of 70.0 to 99.0 wt %.

Within the scope of a further very particularly preferred embodiment, a method according to the invention is characterized in that agent (a)—in relation to the total weight of agent (a)—contains one or more components of the cosmetic carrier (a4) in a total amount of 10.0 to 99.0 wt %, preferably of 30.0 to 99.0 wt %, further preferably of 50.0 to 99.0 wt %, and very particularly preferably of 70.0 to 99.0 wt %.

Within the scope of a further particularly preferred embodiment, a method according to the invention is characterized in that agent (a)—in relation to the total weight of agent (a)—contains one or more constituents (a4) from the group consisting of poly-$C_1$-$C_6$ alkylene glycols, 1,2-propylene glycol, 1,3-propylene glycol, 1,2 butylene glycol, dipropylene glycol, ethanol, isopropanol, diethylene glycol monoethyl ether, glycerol, phenoxyethanol, and benzyl alcohol in a total amount of 10.0 to 99.0 wt %, preferably of 30.0 to 99.0 wt %, further preferably of 50.0 to 99.0 wt %, and very particularly preferably of 70.0 to 99.0 wt %.

In the context of a further, explicitly, very particularly preferred embodiment, a method according to the invention is characterized in that agent (a)—in relation to the total weight of agent (a)—contains one or more alkylene glycols (a4) of the formula (AG) in a total amount of 10.0 to 99.0 wt %, preferably of 30.0 to 99.0 wt %, further preferably of 50.0 to 99.0 wt %, and very particularly preferably of 70.0 to 99.0 wt %.

It is understood here that the sum of all the ingredients, present in the agents (a), from the groups (a1), (a2), (a3), and in some cases (a4) can be no more than 100 wt %. If further, optional ingredients are to be used in the agent, the total sum of the aforementioned ingredients is reduced by a corresponding extent to values of less than 100 wt %.

Step (2), Applying Agent (b) to the Keratinous Material

In the second step of the method according to the invention, agent (b) is applied to the keratinous material or the hair, which is still impinged with agent (a). Step (2) occurs after step (1), i.e., after agent (a) has been applied completely to the keratinous material, agent (b) is applied. The successive application of the two agents (a) and (b) takes place within a period of one hour, and preferably within 30 minutes. Agent (b) is very particularly preferably applied within 10 minutes, and very particularly preferably within 5 minutes, after application of agent (a) to the keratinous material. An application of agent (b) within 10 minutes means that the application of agent (b) is started within a period of no more than 10 minutes after the application of agent (a) to the keratinous material has been completed.

In the context of a further particularly preferred embodiment, a method according to the invention is characterized by the application of agent (b) within 10 minutes, and preferably within 5 minutes, after application of agent (a).

By applying agent (b), a mixture of agents (a) and (b) is produced at the locations of the keratinous material which are impinged with agent (a). Agent (b) contains a defined amount of water (b1), which results in the silanes now present on the keratinous material (a2) undergoing the oligomerization or polymerization reaction, which leads to the formation of the colored film. It is therefore essential for the method according to the invention to form the mixture of (a) and (b) at all the sites of the keratinous material which are to be colored.

By mixing agents (a) and (b), the two agents are also emulsified, so that the silanes (a2) and the amount of water (b1) initiating the polymerization come into direct contact with one another. The mixing can take place, for example, manually with the gloved hand and by massaging or working the two agents into the keratinous material.

In the context of a further particularly preferred embodiment, a method according to the invention is therefore characterized by the (2) application of an agent (b) to the keratinous material, which is still impinged with agent (a), and production of a mixture of the two agents (a) and (b) on the keratinous material by manually mixing the two agents.

The water contained in agent (b) initiates the polymerization. For this purpose, the water content in agent (b) is particularly preferably set to certain values. In this context, it has been found to be particularly advantageous if agent (b)—in relation to the total weight of agent (b)—has 10 to 100 wt %, preferably 30 to 99.5 wt %, further preferably 50 to 99 wt %, and very particularly preferably 80 to 99 wt %, water.

In the context of a further particularly preferred embodiment, a method according to the invention is characterized in that agent (b) contains, in relation to the total weight of agent (b), 10 to 100 wt %, preferably 30 to 99.5 wt %, further preferably 50 to 99 wt %, and very particularly preferably 80 to 99 wt %, water.

Thickener in Agent (b)

In order to ensure sufficiently high miscibility of the agents (a) and (b) and to ensure that agent (b) does not drip off the keratinous material or the hair after the application, agent (b) can additionally contain a thickening agent.

In the context of a further particularly preferred embodiment, a method according to the invention is characterized in that agent (b) contains at least one thickener.

Suitable thickeners include, for example, chemically-modified celluloses, such as propyl cellulose, methyl ethyl cellulose, carboxymethyl cellulose, hydroxyethyl cellulose, methylhydroxy ethyl cellulose, ethylhydroxy ethyl cellulose, hydroxypropyl cellulose, hydroxypropyl methyl cellulose, carboxymethyl hydroxyethyl cellulose, sulfoethyl cellulose, carboxymethyl sulfoethyl cellulose, hydroxypropyl sulfoethyl cellulose, hydroxyethyl sulfoethyl cellulose, methylethyl hydroxyethyl cellulose, methylosulfoethyl cellulose, and/or ethylsulfoethyl cellulose.

In a preferred embodiment, a method for coloring keratinous material is characterized in that agent (b) further contains a thickener selected from the group consisting of propyl cellulose, methyl ethyl cellulose, carboxymethyl cellulose, hydroxyethyl cellulose, methyl hydroxyethyl cellulose, ethylhydroxyethyl cellulose, hydroxypropyl cellulose, hydroxypropyl methyl cellulose, carboxymethyl hydroxyethyl cellulose, sulfoethyl cellulose, carboxymethyl sulfoethyl cellulose, hydroxypropyl sulfoethyl cellulose, hydroxyethyl sulfoethyl cellulose, methyl ethyl hydroxyethyl cellulose, methylsulfoethyl cellulose, ethylsulfoethyl cellulose, and mixtures thereof.

Particularly suitable thickeners are selected from hydroxyethyl cellulose, hydroxypropyl cellulose, hydroxypropyl methyl cellulose, and mixtures thereof.

Further suitable thickeners include galactomannans. Preferred galactomannans include galactomannans with the INCI designation *Cyamopsis tetragonoloba* gum (guar gum), galactomannans with the INCI designation *Ceratonia siliqua* (carob) gum (locust bean gum), galactomannans with the INCI designation *Cassia* gum, and galactomannans with the INCI designation *Caesalpinia spinosa* gum (tara gum).

Accordingly, a method for coloring keratinous material is particularly preferred in which agent (b) further contains at least one galactomannan which is selected from the group consisting of galactomannans with the INCI designation *Cyamopsis tetragonoloba* Gum (guar gum), galactomannans with the INCI designation *Ceratonia siliqua* (carob) gum (locust bean gum), galactomannans with the INCI designation *Cassia* gum, and galactomannans with the INCI designation *Caesalpinia spinosa* gum (tara gum). In a particularly preferred embodiment, the galactomannan comprises a galactomannans with the INCI designation *Caesalpinia spinosa* gum (tara gum).

The amount of thickener is preferably between 0.1 and 10 wt %, in each case in relation to the total amount of agent (b).

Further Ingredients in Agents (a) and (b)

The agents (a) and (b) described above may further contain one or more optional ingredients.

The cosmetic ingredients which can optionally be used in agent (a) can be all suitable components for giving the agent further positive properties. For example, one or more compounds having an active surface area from the group of nonionic, cationic, anionic, or zwitterionic/amphoteric surfactants can additionally be contained in agent (a) and/or (b), The agents can also contain further active substances, auxiliary substances, and additives, such as solvents, fatty constituents of, for example, $C_8$-$C_{30}$ fatty acid triglycerides, $C_8$-$C_{30}$ fatty acid monoglycerides, $C_8$-$C_{30}$ fatty acid diglycerides, and/or the hydrocarbons; structurants, such as glucose, maleic acid, and lactic acid, hair-conditioning compounds such as phospholipids, e.g., lecithin and cephalins; perfume oils, dimethyl isosorbide, and cyclodextrins; fiber-structure-improving active substances—in particular, mono-, di-, and oligosaccharides, such as glucose, galactose, fructose, fruit sugar, and lactose; dyes for coloring the agent; anti-dandruff active substances, such as piroctone olamine, zinc omadine, and climbazole; amino acids and oligopeptides; animal-based and plant-based protein hydrolysates as well as derivatives in the form of the fatty acid condensation products thereof or, where appropriate, anionically or cationically modified; vegetable oils; light protection agents and UV blockers; active substances such as panthenol, pantothenic acid, pantolactone, allantoin, pyrrolidinone carboxylic acids, and the salts thereof, as well as bisabolol; polyphenols—in particular, hydroxy cinnamic acids, 6,7-dihydroxycoumarins, hydroxybenzoic acids, catechins, tannins, leucoanthocyanidins, anthocyanidins, flavanones, flavones, and flavonols; ceramides or pseudoceramides; vitamins, provitamins, and vitamin precursors; plant extracts; fats and waxes, such as fatty alcohols, beeswax, montan wax, and paraffins; bulking agents and penetration substances, such as glycerol, propylene glycol monoethyl ether, carbonates, hydrogen carbonates, guanidines, ureas, and primary, secondary, and tertiary phosphates; opacifiers, such as latex, styrene/PVP, and styrene/acrylamide copolymers; pearlescent agents, such as ethylene glycol mono- and distearate and PEG-3 distearate; and propellants, such as propane-butane mixtures, $N_2O$, dimethyl ether, $CO_2$, and air.

The selection of these additional substances is made by a person skilled in the art according to the desired properties of the agents. With regard to other optional components and the amounts of said components used, reference is explicitly made to relevant reference books known to a person skilled in the art. The additional active ingredients and auxiliaries are used in the preparations according to the invention preferably in each case in amounts of 0.0001 to 25 wt %, and in particular of 0.0005 to 15 wt %, in relation to the total weight of the respective agent.

Step (3), Allowing Both Agents (a) and (b) to Act Upon the Keratinous Material

After the two agents (a) and (b) are mixed with one another, the mixture thereof is allowed to act upon all the parts of the keratinous material which are impinged with the mixture of both agents.

With the mixing of the two agents (a) and (b), the silanes (a2) contained in agent (a) are brought into contact with the defined amount of water (b1) present in agent (b), such that a hydrolysis and oligomerization or polymerization of the silanes (a2) is initiated. The coating or film is formed in this way at exactly the locations of the keratinous material which are wetted with the mixture of both agents (a) and (b). The extent and speed of the hydrolysis or of the polymerization are determined here by the ratio of the amounts of silane (a2) and amounts of water (b1) on the hair. The smaller the quantitative ratio of (a2) to (b1), i.e., the quantitative ratio (a2)/(b) 1), the more water is available for a certain amount of silane and the faster and more comprehensively the polymerization proceeds. The quantitative ratio (a2)/(b1) can now be determined on the one hand by the amount of both agents (a) and (b) which are each applied to the keratinous materials or hair. Further factors are the concentration of the silanes (a2) in agent (a) and the water concentration in agent (b). In this connection, it has been found that the oligomerization or polymerization could then be adjusted to the optimum rate for the application if the weight ratio of the total amount of the organic silicon compounds (a2) present in agent (a) to the amount of the water (b1) contained in agent (b), i.e., the weight ratio (a2)/(b1) is of a value of 1:100 to 1:1, preferably of 1:70 to 1:2, more preferably of 1:70 to 1:5, and very particularly preferably of 1:70 to 1:10.

In other words, it was possible to produce a particularly uniform and resistant film on the keratinous material if both the amounts of agents (a) and (b) and the concentrations of the silanes (a2) and of the water (b1) in the two agents were selected such that the silanes (a2) and the water (b1) were present on the keratinous material in a weight ratio of 1:100 to 1:1, preferably of 1:70 to 1:2, more preferably of 1:70 to 1:5, and very particularly preferably of 1:70 to 1:10.

A weight ratio (a2)/(b1) of 1:70 to 1:10 means here that the water (b1) originating from agent (b), compared to the total amount of the silanes (a2) originating from agent (a), is applied to produce a 10-fold to 70-fold excess weight.

EXAMPLE 40 g of agent (a) are applied to the hair of a subject; agent (a) is briefly massaged into the entire hair mass.

Agent (a) contains 1.0 wt % water (a1) (or a mixture of water and acid or a mixture of water and alkaline solution), 3.0 wt % 3-(aminopropyl)triethoxysilane (a2), 6.0 wt % methyltriethoxysilane (a2), 1.0 wt % pigment (e.g., Unipure Red LC3079), 89 wt % polyethylene glycol (e.g., PEG-8).

The total amount of the silanes (a2) contained in agent (a) is 3.6 g, i.e., 1.2 g 3-(aminopropyl)-triethoxysilane and 2.4 g methyltriethoxysilane.

After the application of agent (a), 100 g of agent (b) are now applied. The agent (b) is a thickened aqueous solution having a water content of 99 wt %. Agent (b) is likewise distributed uniformly over the entire head of the subject.

After application of agent (b), the hair is vigorously massaged for 1 minute with the fingers, so that both agents (a) and (b) are completely mixed with one another.

99 g of water (b1) are present in agent (b).

The weight ratio of the total amount of the organic silicon compounds (a2) contained in agent (a) to the amount of the water (b1) contained in agent (b), i.e., the weight ratio (a2)/(b1), is 3.6:99=1:27.5.

In the context of an explicitly very particularly preferred embodiment, a method according to the invention is characterized in that the weight ratio of the total amount of the organic silicon compounds (a2) contained in agent (a) to the amount of the water (b1) contained in agent (b), i.e., the weight ratio (a2)/(b1), is of a value of 1:100 to 1:1, preferably of 1:70 to 1:2, more preferably of 1:70 to 1:5, and very particularly preferably of 1:70 to 1:10.

After the two agents (a) and (b) are mixed, both agents are now allowed to act together in the form of their mixture upon the keratinous material. Preferably, both agents (a) and (b) are allowed to act together upon the keratinous material, and in particular on the human hair, for a period of 10 seconds to 30 minutes, preferably of 30 seconds to 20 minutes, more preferably of 1 minute to 15 minutes, and most particularly of 5 minutes to 10 minutes.

In the context of a further preferred embodiment, a method according to the invention is characterized by (3) allowing the two agents (a) and (b) to act together upon the keratinous material for a period of time of 10 seconds to 30 minutes, preferably of 30 seconds to 20 minutes, more preferably of 1 minute to 15 minutes, and most particularly of 5 minutes to 10 minutes.

Step (4), Rinsing Out Both Agents (a) and (b)

The work leading to this invention has shown that, after the lapse of the exposure time in step (3) of the method, a colored film has formed which is distinguished by particularly high uniformity. When used on hair in the form of a whole-head application, the entire head could thus be colored with a uniform color result. After the action of the two agents (a) and (b), they could then be rinsed off again from the keratinous material or rinsed out of the hair.

Step (4) of the method according to the invention therefore comprises rinsing out both agents (a) and (b). The two agents (a) and (b) are preferably rinsed out under running water.

In the context of a further preferred embodiment, a method according to the invention is characterized by (4) rinsing out both agents (a) and (b) under running water.

Examples

The following formulations were prepared (unless stated otherwise, all figures are in wt %)

Agent (a)

| Agent (a) | wt % |
|---|---|
| (3-aminopropyl)triethoxysilane (a2) | 3.0 |
| methyltriethoxysilane (a2) | 6.0 |
| water (a1) | 1.0 |
| NaOH | 0.01 |
| Unipure Red LC 3079 (Pigment Red 7, CAS-No. 5281-04-9) (a3) | 1.0 |
| PEG-8 (polyethylene glycol, molecular weight 400 g/mol) | up to 100 |

Agent (b)

| Agent (b) | wt % |
|---|---|
| water | 99.0 |
| hydroxyethyl cellulose (Natrosol 250 HR) | 1.0 |

5 strands of hair (Kerling natural white) were dampened under running water and then rubbed dry with a hand towel for 30 seconds. Agent (a) was then applied to all the towel-dry strands of hair (0.4 g of agent (a) per strand of hair). Agent (a) was massaged into all of the strands of hair for 30 seconds. Directly thereafter, agent (b) was applied to the strands of hair (1.0 g agent (b) per strand of hair). Each strand of hair was massaged again for 30 seconds, so that a mixture of agents (a) and (b) was formed.

0.036 g of silanes (a2) were applied to the hair.

0.99 g of water (b1) were applied from the hair.

The weight ratio (a2)/(b1) was 0.036:0.99=1:27.5

This mixture of agents (a) and (b) was allowed to act upon the strands of hair for 5 minutes. The strands of hair were then rinsed under running water and dried. A uniform and intense coloration was obtained. In this process, all 5 strands of hair had the same red coloration and had an equally high color intensity.

Comparison 5 strands of hair (Kerling natural white) were dampened under running water and then rubbed dry for 30 seconds with a hand towel. Then, 40 g of agent (a) were mixed with 100 g of agent (b). This application mixture was applied to 5 strands of hair (in each case, 1.4 g of application mixture per strand of hair). Each strand of hair was massaged for 30 seconds. The application mixture was then in each case allowed to act for 5 minutes upon all the strands of hair. The strand of hair was then rinsed under running water and dried. All strands of hair were dyed red. However, the strand of hair which was colored first had a higher color intensity than the strand of hair which was last treated with the mixture of (a) and (b).

The invention claimed is:

1. A method for dyeing keratinous material, the method comprising:

applying a first agent to the keratinous material, wherein the first agent comprises:

water present in an amount less than 10 wt %, based on the total weight of the first agent, at least one organic silicon compound selected from the group of silanes having one, two, or three silicon atoms, at least one chromophoric compound, and at least one cosmetic carrier present in an amount of from 70 wt % to 90 wt %, based on the total weight of the first agent, wherein the at least one cosmetic carrier has the structure of formula (AG):

$$H-O-[CH_2-CH_2-O]_x-H, \quad \text{(AG)}$$

wherein x represents an integer from 2 to 800;

applying a second agent to the keratinous material while still impinged with the first agent, wherein the second agent comprises water;

allowing the first agent and the second agent to act upon the keratinous material; and rinsing the first agent and the second agent.

2. The method of claim 1, wherein the first agent is applied to dry keratinous material.

3. The method of claim 1, wherein the at least one organic silicon compound has the structure of formula (I) and/or (II):

$$R_1R_2N\text{-}L\text{-}Si(OR_3)_a(R_4)_b \quad \text{(I)},$$

wherein:

$R_1$ and $R_2$ represent, independently of one another, a hydrogen atom or a $C_1$-$C_6$ alkyl group, L represents a linear or branched, bivalent $C_1$-$C_{20}$ alkylene group, $R_3$ and $R_4$ represent, independently of one another, a $C_1$-$C_6$ alkyl group, a represents an integer from 1 to 3, and b represents the integer 3-a, and $$(R_5O)_c(R_6)_dSi\text{-}(A)_e\text{-}[NR_7\text{-}(A')]_f-[O\text{-}(A'')]_g-[NR_8\text{-}(A''')]_h-Si(R_{6'})_{d'}(OR_{5'})_{c'} \quad \text{(II)},$$

wherein:

R5, R5', R5", R6, R6', and R6" represent, independently of one another, a $C_1$-$C_6$ alkyl group, A, A', A", A"', and A"" represent, independently of one another, a linear or branched, bivalent $C_1$-$C_{20}$ alkylene group, and $R_7$ and $R_8$ represent, independently of one another, a hydrogen atom, a $C_1$-$C_6$ alkyl group, a hydroxy-$C_1$-$C_6$ alkyl group, a $C_2$-$C_6$ alkenyl group, an amino-$C_1$-$C_6$ alkyl group, or a group having a structure of formula (III):

$$(A'''')-Si(R_6'')_d''(OR_5'')_c'' \quad \text{(III)},$$

wherein:

c represents an integer from 1 to 3, d represents the integer 3-c, c' represents an integer from 1 to 3, d' represents the integer 3-c', c" represents an integer from 1 to 3, d" represents the integer 3-c", e represents 0 or 1, f represents 0 or 1, g represents 0 or 1, and h represents 0 or 1, wherein at least one of the functional groups e, f, g, and h is different from 0.

4. The method of claim 1, wherein the at least one organic silicon compound has a structure of formula (I), $$R_1R_2N\text{-}L\text{-}Si(OR_3)_a(R_4)_b \quad \text{(I)},$$

wherein:

$R_1$ and $R_2$ both represent a hydrogen atom,

L represents a linear, bivalent $C_1$-$C_6$ alkylene group, $R_3$ and $R_4$ represent, independently of one another, a methyl group or an ethyl group, a represents the number 3, and b represents the number 0.

5. The method of claim 1, wherein the at least one organic silicon compound is selected from the group consisting of:

(3-aminopropyl)triethoxysilane,
(3-aminopropyl) trimethoxysilane,
1-(3-aminopropyl) silanetriol,
(2-aminoethyl)triethoxysilane,
(2-aminoethyl)trimethoxysilane,
1-(2-aminoethyl) silanetriol,
(3-dimethylaminopropyl)triethoxysilane,
(3-dimethylaminopropyl) trimethoxysilane,
1-(3-dimethylaminopropyl) silanetriol,
(2-dimethylaminoethyl)triethoxysilane,
(2-dimethylaminoethyl)trimethoxysilane, and
1-(2-dimethylaminoethyl) silanetriol.

6. The method of claim 1, wherein the at least one organic silicon compound has a structure of formula (IV):

$$R_9Si(OR_{10})_k(R_{11})_m \quad (IV),$$

wherein:

$R_9$ represents a $C_1$-$C_{18}$ alkyl group, $R_{10}$ represents a hydrogen atom or a $C_1$-$C_6$ alkyl group, $R_{11}$ represents a $C_1$-$C_6$ alkyl group, k represents an integer from 1 to 3, and m represents the integer 3-k.

7. The method of claim 1, wherein the at least one organic silicon compound is selected from the group consisting of:

methyltrimethoxysilane,
methyltriethoxysilane,
ethyltrimethoxysilane,
ethyltriethoxysilane,
propyltrimethoxysilane,
propyltriethoxysilane,
hexyltrimethoxysilane,
hexyltriethoxysilane,
octyltrimethoxysilane,
octyltriethoxysilane,
dodecyltrimethoxysilane,
dodecyltriethoxysilane,
octadecyltrimethoxysilane, and
octadecyltriethoxysilane.

8. The method of claim 1, wherein the at least one organic silicon compound comprises at least two, structurally different from one another, organic silicon compounds.

9. The method of claim 1, wherein the at least one organic silicon compound is present in an amount of from 0.1 wt % to 20 wt %, based on the total weight of the first agent.

10. The method of claim 1, wherein the at least one chromophoric compound is selected from the group consisting of pigments and direct dyes.

11. The method of claim 1, wherein the first agent further comprises at least one inorganic pigment selected from the group consisting of chromophoric metal oxides, metal hydroxides, metal oxide hydrates, silicates, metal sulfides, complex metal cyanides, metal sulphates, bronze pigments, and mica-based colored pigments coated with at least one metal oxide or metal oxychloride.

12. The method of claim 1, wherein the first agent further comprises at least one organic pigment selected from the group consisting of carmine, quinacridone, phthalocyanine, sorghum, blue pigments with the Color Index numbers CI 42090, CI 69800, CI 69825, CI 73000, CI 74100, or CI 74160, yellow pigments with the Color Index numbers CI 11680, CI 11710, CI 15985, CI 19140, CI 20040, CI 21100, CI 21108, CI 47000, or CI 47005, green pigments with the Color Index numbers CI 61565, CI 61570, or CI 74260, orange pigments with the Color Index numbers CI 11725, CI 15510, CI 45370, or CI 71105, and red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915, or CI 75470.

13. The method of claim 1, wherein the at least one chromophoric compound is selected from the group consisting of pigments based upon a lamellar substrate plate, pigments based upon a lenticular substrate plate, and vacuum-metalized pigments.

14. The method of claim 1, wherein the second agent is applied within 10 minutes after application of the first agent.

15. The method of claim 1, wherein the water in the second agent is present in an amount of from 10 to 100 wt %, based on the total weight of the second agent.

16. The method of claim 1, wherein the second agent further comprises at least one thickener.

17. The method of claim 1, wherein the weight ratio of the total amount of the at least one organic silicon compound in the first agent to the amount of the water in the second agent is from 1:100 to 1:1.

18. The method of claim 1, wherein allowing the first agent and the second agent to act on the keratinous material is for a period of time of from 10 seconds to 30 minutes.

19. The method of claim 1, wherein the at least one cosmetic carrier is polyethylene glycol having a molecular mass of from 200 g/mol to 400 g/mol.

20. The method of claim 1, wherein at the at least one cosmetic carrier is selected from the group consisting of polyethylene glycol-6, polyethylene glycol-7, polyethylene glycol-9, and polyethylene glycol-10.

* * * * *